United States Patent [19]
Dean et al.

[11] Patent Number: 5,925,331
[45] Date of Patent: Jul. 20, 1999

[54] TECHNETIUM-99M LABELED PEPTIDES FOR THROMBUS IMAGING

[75] Inventors: Richard T. Dean; John Lister-James, both of Bedford, N.H.

[73] Assignee: Diatide, Inc., Londonderry, N.H.

[21] Appl. No.: 08/335,832

[22] PCT Filed: May 21, 1993

[86] PCT No.: PCT/US93/04794

§ 371 Date: Jan. 5, 1995

§ 102(e) Date: Jan. 5, 1995

[87] PCT Pub. No.: WO93/23085

PCT Pub. Date: Nov. 25, 1993

Related U.S. Application Data

[63] Continuation-in-part of application No. 08/886,752, May 21, 1992, abandoned.

[51] Int. Cl.$^6$ .......................... A61K 51/08; A61K 35/14; C07F 13/00
[52] U.S. Cl. .......................... 424/1.69; 534/14; 530/380; 530/382; 530/331
[58] Field of Search ..................... 530/323, 331, 530/332, 334, 336, 317, 381, 382, 380; 930/24, 30; 424/1.69, 1.41, 1.49; 534/14

[56] References Cited

U.S. PATENT DOCUMENTS

| | | |
|---|---|---|
| 4,578,079 | 3/1986 | Ruoslahti et al. . |
| 4,792,525 | 12/1988 | Ruoslahti et al. . |
| 4,957,903 | 9/1990 | Ranby ........................................ 514/18 |
| 5,371,184 | 12/1994 | Rajagopalan et al. .................. 530/324 |
| 5,443,816 | 8/1995 | Zamora et al. ......................... 424/1.69 |

FOREIGN PATENT DOCUMENTS

| | | |
|---|---|---|
| 823017009 | 3/1982 | European Pat. Off. ....... A61K 49/02 |
| 823017009 | 10/1982 | European Pat. Off. . |
| 85104959 | 12/1985 | European Pat. Off. . |
| 91301948 | 10/1991 | European Pat. Off. . |
| 8900051 | 1/1988 | WIPO ............................. A61K 43/00 |
| 8902752 | 9/1988 | WIPO ............................. A61K 49/00 |
| 8802276 | 1/1989 | WIPO . |
| 8903318 | 4/1989 | WIPO . |
| 8910135 | 4/1989 | WIPO ............................. A61K 37/02 |
| 8912680 | 6/1989 | WIPO ............................. C12N 9/48 |
| 8901742 | 11/1989 | WIPO . |
| 8901827 | 11/1989 | WIPO . |
| 8902656 | 12/1989 | WIPO . |
| 9015818 | 6/1990 | WIPO ............................. C07K 5/08 |
| 9102750 | 8/1990 | WIPO ............................. C07K 7/10 |
| WO9010463 | 9/1990 | WIPO . |
| 9000933 | 12/1990 | WIPO . |
| 9003788 | 2/1991 | WIPO . |
| 9004642 | 3/1991 | WIPO . |
| 9117173 | 5/1991 | WIPO ............................. C07H 21/00 |
| 9101331 | 7/1991 | WIPO ............................. C07K 7/54 |
| 9103116 | 11/1991 | WIPO . |
| 9106479 | 4/1992 | WIPO . |

OTHER PUBLICATIONS

* Knight, 1990, "Radiopharmceuticals for Thrombus Detection", Sem. Nucl. Med. 20:52–67.

Baidoo & Lever, 1990, "Synthesis of a Diaminedithiol Bifunctional Chelating Agent for Incorporation of Technetium–99m into Biomolecules", *Bioconjugate Chem.* 1: 132–137.

Bryson et al., 1990, "Protecting Groups in the Preparation of Thiolate Complexes of Technetium", *Inorganic Chem.* 29: 2948–2951.

*Primary Examiner*—Gary E. Hollinden
*Assistant Examiner*—Michael G. Hartley
*Attorney, Agent, or Firm*—McDonnell Boehnen Hulbert & Berghoff

[57] ABSTRACT

This invention relates to radiolabeled reagents that are scintigraphic imaging agents for imaging sites of thrombus formation in vivo, and methods for producing such reagents. Specifically, the invention relates to reagents each comprised of a specific binding compound, capable of binding to at least one component of a thrombus, covalently linked to a radiolabel-binding moiety. The invention provides these reagents, methods and kits for making such reagents, and methods for using such reagents labeled with technetium-99m to image thrombus sites in a mammalian body.

39 Claims, 1 Drawing Sheet

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
      (A) LENGTH: 8 amino acids

```
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..5
        (D) OTHER INFORMATION: /label= thioether
            /note= "The sidechain sulfur of the C-terminal
            cysteine residue is covalently linked as an ether
            to the group [CH2CO], which group forms an amide
            bond with the N-terminal D-tyrosine residue"

(ix) FEATURE:
        (A) NAME/KEY: Modified-site
        (B) LOCATION: 6
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur atom by covalent linkage to an
            acetamido group"

(ix) FEATURE:
        (A) NAME/KEY: Modified-site
        (B) LOCATION: 8
        (D) OTHER INFORMATION: /label= Amide
            /note= "The carboxyl terminus is modified to an
            amide"

(xi) SEQUENCE DESCRIPTION: SEQ ID NO:1:

Tyr Arg Gly Asp Cys Cys Gly Cys
    1               5

(2) INFORMATION FOR SEQ ID NO:2:

(i) SEQUENCE CHARACTERISTICS:
         (A) LENGTH: 11 amino acids
         (B) TYPE: amino acid
         (D) TOPOLOGY: circular (ii) MOLECULE TYPE: peptide (ix) FEATURE:
         (A) NAME/KEY: Cross-links
         (B) LOCATION: 1..5
         (D) OTHER INFORMATION: /label= thioether
             /note= "The sidechain sulfur atom of the cysteine
             residue is covalently linked to the group [CH2CO],
             which group forms an amide bond with the N-terminal
             D-tyrosine"

(ix) FEATURE:
         (A) NAME/KEY: Modified-site
         (B) LOCATION: 9
         (D) OTHER INFORMATION: /label= Acm
             /note= "This cysteine residue is blocked at the
             sidechain sulfur by covalent linkage to an
             acetamido group"

(ix) FEATURE:
         (A) NAME/KEY: Modified-site
         (B) LOCATION: 11
         (D) OTHER INFORMATION: /label= Acm
             /note= "This cysteine residue is blocked at the
             sidechain sulfur atom by covalent linkage to an
             acetamido group"

(ix) FEATURE:
         (A) NAME/KEY: Modified-site
         (B) LOCATION: 11
```

(D) OTHER INFORMATION: /label= Amide
                        /note= "The carboxyl terminus is modified to an
                        amide"

(xi) SEQUENCE DESCRIPTION: SEQ ID NO:2:

Tyr Arg Gly Asp Cys Trp Gly Gly Cys Gly Cys
        1               5                   10

(2) INFORMATION FOR SEQ ID NO:3:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1..5
            (D) OTHER INFORMATION: /label= thioether
                /note= "The sidechain sulfur atom of the cysteine
                residue is covalently linked to the group [CH2CO]
                to form a thioether, and the [CH2CO] group is covalently
                linked to the N-terminal D-tyrosine to form an amide
                bond."

(ix) FEATURE:
            (A) NAME/KEY: Modified-site
            (B) LOCATION: 9
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 11
            (D) OTHER INFORMATION: /label= Acm
                /note= "This cysteine residue is blocked at the
                sidechain sulfur atom by covalent linkage to an
                acetamido group"

(ix) FEATURE:
            (A) NAME/KEY: Modified-site
            (B) LOCATION: 11
            (D) OTHER INFORMATION: /label= Amide
                /note= "The carboxyl terminus is modified to an
                amide"

(xi) SEQUENCE DESCRIPTION: SEQ ID NO:3:

Tyr Arg Gly Asp Cys Phe Gly Gly Cys Gly Cys
        1               5                   10

(2) INFORMATION FOR SEQ ID NO:4:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1..5
            (D) OTHER INFORMATION: /label= thioether
                /note= "The sidechain sulfur atom of the cysteine
                is covalently linked to the group [CH2CO] to form
                a thioether; the [CH2CO] group is further linked
                to the N-terminal D-tyrosine to form an amide bond."

(ix) FEATURE:
            (A) NAME/KEY: Modified-site
            (B) LOCATION: 9
            (D) OTHER INFORMATION: /label= Acm

```
           /note= "This cysteine residue is blocked at the
           sidechain sulfur by covalent linkage to an
           acetamido group"

(ix) FEATURE:
     (A) NAME/KEY: Modified-site
     (B) LOCATION: 11
     (D) OTHER INFORMATION: /label= Acm
           /note= "This cysteine residue is blocked at the
           sidechain sulfur atom by covalent linkage to an
           acetamido group"

(ix) FEATURE:
     (A) NAME/KEY: Modified-site
     (B) LOCATION: 11
     (D) OTHER INFORMATION: /label= Amide
           /note= "The carboxyl terminus is modified to an
           amide"

(xi) SEQUENCE DESCRIPTION: SEQ ID NO:4:

Tyr Arg Gly Asp Cys Gly Gly Gly Cys Gly Cys
1               5                   10

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: circular (ii) MOLECULE TYPE: peptide (ix) FEATURE:
        (A) NAME/KEY: Cross-links
        (B) LOCATION: 1..5
        (D) OTHER INFORMATION: /label= thioether
              /note= "The sidechain sulfur atom of the cysteine
              is covalently linked to the group [CH2CO] to form
              a thioether; said group is further covalently
              linked to the N-terminal D-tyrosine to form an amide
              bond."

(ix) FEATURE:
        (A) NAME/KEY: Modified-site
        (B) LOCATION: 9
        (D) OTHER INFORMATION: /label= Acm
              /note= "This cysteine residue is blocked at the
              sidechain sulfur by covalent linkage to an
              acetamido group"

(ix) FEATURE:
        (A) NAME/KEY: Modified-site
        (B) LOCATION: 11
        (D) OTHER INFORMATION: /label= Acm
              /note= "This cysteine residue is blocked at the
              sidechain sulfur atom by covalent linkage to an
              acetamido group"

(ix) FEATURE:
        (A) NAME/KEY: Modified-site
        (B) LOCATION: 11
        (D) OTHER INFORMATION: /label= Amide
              /note= "The carboxyl terminus is modified to an
              amide"

(xi) SEQUENCE DESCRIPTION: SEQ ID NO:5:

Tyr Arg Gly Asp Cys Asp Gly Gly Cys Gly Cys
   1               5                   10

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: circular
```

(ii) MOLECULE TYPE: peptide (ix) FEATURE:
              (A) NAME/KEY: Cross-links
              (B) LOCATION: 1
              (D) OTHER INFORMATION: /label= thioether
                    /note= "The sulfur in the first cysteine is
                    covalently linked to a [3-aminopropyl group; the
                    sulfur of the second cysteine is linked to a
                    [CH2CO] group to form a thioether, and said
                    [CH2CO] group is further covalently linked
                    to the N-terminal D-tyrosine to form an amide bond."

(ix) FEATURE:
              (A) NAME/KEY: Modified-site
              (B) LOCATION: 9
              (D) OTHER INFORMATION: /label= Acm
                    /note= "This cysteine residue is blocked at the
                    sidechain sulfur by covalent linkage to an
                    acetamido group"

(ix) FEATURE:
              (A) NAME/KEY: Modified-site
              (B) LOCATION: 11
              (D) OTHER INFORMATION: /label= Acm
                    /note= "This cysteine residue is blocked at the
                    sidechain sulfur atom by covalent linkage to an
                    acetamido group"

(ix) FEATURE:
              (A) NAME/KEY: Modified-site
              (B) LOCATION: 11
              (D) OTHER INFORMATION: /label= Amide
                    /note= "The carboxyl terminus is modified to an
                    amide"

(xi) SEQUENCE DESCRIPTION: SEQ ID NO:6:

Tyr Cys Gly Asp Cys Gly Gly Gly Cys Gly Cys
        1               5                   10

(2) INFORMATION FOR SEQ ID NO:7:

(i) SEQUENCE CHARACTERISTICS:
              (A) LENGTH: 11 amino acids
              (B) TYPE: amino acid
              (D) TOPOLOGY: circular (ii) MOLECULE TYPE: peptide (ix) FEATURE:
              (A) NAME/KEY: Cross-links
              (B) LOCATION: 1..5
              (D) OTHER INFORMATION: /label= thioether
                    /note= "The sidechain sulfur atom of the cysteine
                    is covalently linked to the group [CH2CO] to form
                    a thioether; the [CH2CO] group is further linked
                    to the N-terminal D-tyrosine to form an amide bond."

(ix) FEATURE:
              (A) NAME/KEY: Modified-site
              (B) LOCATION: 9
              (D) OTHER INFORMATION: /label= Acm
                    /note= "This cysteine residue is blocked at the
                    sidechain sulfur by covalent linkage to an
                    acetamido group"

(ix) FEATURE:
              (A) NAME/KEY: Modified-site
              (B) LOCATION: 11
              (D) OTHER INFORMATION: /label= Acm
                    /note= "This cysteine residue is blocked at the
                    sidechain sulfur atom by covalent linkage to an
                    acetamido group"

(ix) FEATURE:
              (A) NAME/KEY: Modified-site
              (B) LOCATION: 11
              (D) OTHER INFORMATION: /label= Amide /note= "The carboxyl terminus is modified to an
amide"

(xi) SEQUENCE DESCRIPTION: SEQ ID NO:7:

Tyr Arg Gly Lys Cys Gly Gly Gly Cys Gly Cys
1               5                   10

(2) INFORMATION FOR SEQ ID NO:8:

(i) SEQUENCE CHARACTERISTICS:
       (A) LENGTH: 10 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /label= Acetyl
           /note= "The amino terminus is modified by covalent
           linkage to an acetyl group."

(ix) FEATURE:
       (A) NAME/KEY: Modified-site
       (B) LOCATION: 1
       (D) OTHER INFORMATION: /label= Acm
           /note= "This cysteine residue is blocked at the
           sidechain sulfur by covalent linkage to an
           acetamido group"

(ix) FEATURE:
       (A) NAME/KEY: Modified-site
       (B) LOCATION: 3
       (D) OTHER INFORMATION: /label= Acm
           /note= "This cysteine residue is blocked at the
           sidechain sulfur by covalent linkage to an
           acetamido group"

(ix) FEATURE:
       (A) NAME/KEY: Disulfide-bond
       (B) LOCATION: 4...10
       (D) OTHER INFORMATION: /label= disulfide
           /note= "The sidechain sulfur atoms of the cysteine
           residues are linked by a disulfide bond."

(ix) FEATURE:
       (A) NAME/KEY: Modified-site
       (B) LOCATION: 7
       (D) OTHER INFORMATION: /label= Apc
           /note= "The sidechain sulfur of the cysteine
           residue is covalently linked to a [3-aminopropyl]
           group forming a thioether"

(xi) SEQUENCE DESCRIPTION: SEQ ID NO:8:

Cys Gly Cys Cys Asn Pro Cys Gly Asp Cys
1               5                   10

(2) INFORMATION FOR SEQ ID NO:9:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /label= Acm
           /note= "This cysteine residue is blocked at the
           sidechain sulfur by covalent linkage to an
           acetamido group"

(ix) FEATURE:

```
        (A) NAME/KEY: Modified-site
        (B) LOCATION: 3
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:9:

Cys Gly Cys Gly Gly Arg Gly Asp Ser
   1               5

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 3
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:10:

Cys Gly Cys Gly Gly Arg Gly Asp Gly Gly Arg Gly Asp Ser
   1               5                  10

(2) INFORMATION FOR SEQ ID NO:11:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 3
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:11:

Cys Gly Cys Gly Gly Arg Gly Asp Gly Gly Arg Gly Asp Gly Gly Arg
   1               5                  10                  15

Gly Asp Ser (2) INFORMATION FOR SEQ ID NO:12:

(i) SEQUENCE CHARACTERISTICS:
```

(A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:12:

Cys Lys Arg Ala Arg Gly Asp Asp Met Asp Asp Tyr Cys
    1               5                  10

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 3
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:13:

Cys Gly Cys Arg Arg Arg Arg Arg Arg Arg Arg Gly Asp Val
    1               5                  10                  15

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 9
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 9
        (D) OTHER INFORMATION: /label= Amide
            /note= "The carboxyl terminus is modified to an
            amide"

(xi) SEQUENCE DESCRIPTION: SEQ ID NO:14:

Gly Arg Gly Asp Val Lys Cys Gly Cys
    1               5

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 8
        (D) OTHER INFORMATION: /label= Amide
            /note= "The carboxyl terminus is modified to an
            amide"

(xi) SEQUENCE DESCRIPTION: SEQ ID NO:15:

Gly Arg Gly Asp Val Cys Gly Cys
1            5

(2) INFORMATION FOR SEQ ID NO:16:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 13
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 13
        (D) OTHER INFORMATION: /label= Amide
            /note= "The carboxyl terminus is modified to an
            amide"

(xi) SEQUENCE DESCRIPTION: SEQ ID NO:16:

Gly Arg Gly Asp Val Arg Gly Asp Phe Lys Cys Gly Cys
1            5                  10

(2) INFORMATION FOR SEQ ID NO:17:

(i) SEQUENCE CHARACTERISTICS:

```
            (A) LENGTH: 12 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 10
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 12
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 12
            (D) OTHER INFORMATION: /label= Amide
                /note= "The carboxyl terminus is modified to an
                amide"

(xi) SEQUENCE DESCRIPTION: SEQ ID NO:17:

Gly Arg Gly Asp Val Arg Gly Asp Phe Cys Gly Cys
    1               5                   10

(2) INFORMATION FOR SEQ ID NO:18:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= mmp
                /note= "The amino terminus is modified by covalent
                linkage to an 2-mercapto-2-methylproprionic acid group."

(xi) SEQUENCE DESCRIPTION: SEQ ID NO:18:

Gly Gly Gly Arg Gly Asp Phe
    1               5

(2) INFORMATION FOR SEQ ID NO:19:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= Acetyl
                /note= "The amino terminus is modified by covalent
                linkage to an acetyl group."

(ix) FEATURE:
            (A) NAME/KEY: Modified-site
            (B) LOCATION: 4
            (D) OTHER INFORMATION: /label= Apc
                /note= "The sidechain sulfur of the cysteine
                residue is covalently linked to a [3-aminopropyl]
                group forming a thioether"
```

(xi) SEQUENCE DESCRIPTION: SEQ ID NO:19:

Cys Asn Pro Cys Gly Asp Cys
    1               5

(2) INFORMATION FOR SEQ ID NO:20:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:20:

Gly Arg Gly Asp Gly Gly Cys
    1               5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acetyl
            /note= "The amino terminus is modified by covalent
            linkage to an mercaptoacetyl group."

(xi) SEQUENCE DESCRIPTION: SEQ ID NO:21:

Gly Gly Arg Gly Asp Phe
    1               5

(2) INFORMATION FOR SEQ ID NO:22:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= ma
            /note= "The amino terminus is modified by covalent
            linkage to an mercaptoacetyl group; the sulfur atom
            is covalently linked to a benzyl group."

(xi) SEQUENCE DESCRIPTION: SEQ ID NO:22:

Gly Gly Arg Gly Asp Phe
    1               5

(2) INFORMATION FOR SEQ ID NO:23:

(i) SEQUENCE CHARACTERISTICS:
        (A) LENGTH: 9 amino acids
        (B) TYPE: amino acid

```
          (D) TOPOLOGY: linear (ii) MOLECULE TYPE: peptide (xi) SEQUENCE DESCRIPTION: SEQ ID NO:23:

Gly Arg Gly Asp Gly Gly Gly Cys
    1               5

(2) INFORMATION FOR SEQ ID NO:24:

(i) SEQUENCE CHARACTERISTICS:
          (A) LENGTH: 7 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= ma
                /note= "The amino terminus is modified by covalent
                linkage to an mercaptoacetyl group; the sulfur atom
                is covalently linked to an acetamidomethyl group."

(xi) SEQUENCE DESCRIPTION: SEQ ID NO:24:

Gly Gly Gly Arg Gly Asp Phe
    1               5

(2) INFORMATION FOR SEQ ID NO:25:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= ma
                /note= "The amino terminus is modified by covalent
                linkage to an mercaptoacetyl group."

(xi) SEQUENCE DESCRIPTION: SEQ ID NO:25:

Arg Gly Asp Phe
    1

(2) INFORMATION FOR SEQ ID NO:26:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /label= Apc
                /note= "The sidechain sulfur atom is covalently
                linked to a [3-aminopropyl] group to form a
                thioether"

(ix) FEATURE:
          (A) NAME/KEY: Modified-site
          (B) LOCATION: 6
          (D) OTHER INFORMATION: /label= Apc
                /note= "The sidechain sulfur atom is covalently
                linked to a [3-aminopropyl] group to form a
                thioether"
```

```
    (ix) FEATURE:
          (A) NAME/KEY: Modified-site
          (B) LOCATION: 11
          (D) OTHER INFORMATION: /label= Acm
                /note= "This cysteine residue is blocked at the
                sidechain sulfur by covalent linkage to an
                acetamido group"

(ix) FEATURE:
          (A) NAME/KEY: Modified-site
          (B) LOCATION: 13
          (D) OTHER INFORMATION: /label= Acm
                /note= "This cysteine residue is blocked at the
                sidechain sulfur by covalent linkage to an
                acetamido group"

(ix) FEATURE:
          (A) NAME/KEY: Modified-site
          (B) LOCATION: 13
          (D) OTHER INFORMATION: /label= Amide
                /note= "The carboxyl terminus is modified to an
                amide"

(xi) SEQUENCE DESCRIPTION: SEQ ID NO:26:

Gly Cys Gly Asp Val Cys Gly Asp Phe Lys Cys Gly Cys
1               5                   10

(2) INFORMATION FOR SEQ ID NO:27:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= Acetyl
                /note= "The amino terminus is modified by covalent
                linkage to an mercaptoacetyl group."

(ix) FEATURE:
          (A) NAME/KEY: Modified-site
          (B) LOCATION: 2
          (D) OTHER INFORMATION: /label= Apc
                /note= "The sidechain sulfur atom is covalently
                linked to a [3-aminopropyl] group to form a
                thioether"

(ix) FEATURE:
          (A) NAME/KEY: Modified-site
          (B) LOCATION: 6
          (D) OTHER INFORMATION: /label= Apc
                /note= "The sidechain sulfur atom is covalently
                linked to a [3-aminopropyl] group to form a
                thioether"

(ix) FEATURE:
          (A) NAME/KEY: Modified-site
          (B) LOCATION: 11
          (D) OTHER INFORMATION: /label= Acm
                /note= "This cysteine residue is blocked at the
                sidechain sulfur by covalent linkage to an
                acetamido group"

(ix) FEATURE:
          (A) NAME/KEY: Modified-site
          (B) LOCATION: 13
          (D) OTHER INFORMATION: /label= Acm
                /note= "This cysteine residue is blocked at the
                sidechain sulfur by covalent linkage to an
                acetamido group"

(ix) FEATURE:
          (A) NAME/KEY: Modified-site
          (B) LOCATION: 13
```

(D) OTHER INFORMATION: /label= Amide
              /note= "The carboxyl terminus is modified to an
              amide"

(xi) SEQUENCE DESCRIPTION: SEQ ID NO:27:

Gly Cys Gly Asp Val Cys Gly Asp Phe Lys Cys Gly Cys
    1               5                   10

(2) INFORMATION FOR SEQ ID NO:28:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= BAT
             /note= "The amino terminus is modified by covalent
             linkage to a BAT group."

(ix) FEATURE:
         (A) NAME/KEY: Modified-site
         (B) LOCATION: 1
         (D) OTHER INFORMATION: /label= Hly
             /note= "This residue is homolysine."

(ix) FEATURE:
         (A) NAME/KEY: Modified-site
         (B) LOCATION: 5
         (D) OTHER INFORMATION: /label= Hly
             /note= "This residue is homolysine."

(ix) FEATURE:
         (A) NAME/KEY: Modified-site
         (B) LOCATION: 8
         (D) OTHER INFORMATION: /label= Amide
             /note= "The carboxyl terminus is modified to an
             amide"

(xi) SEQUENCE DESCRIPTION: SEQ ID NO:28:

Xaa Gly Asp Pro Xaa Gly Asp Phe
    1               5

(2) INFORMATION FOR SEQ ID NO:29:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= Acm
             /note= "This cysteine residue is blocked at the
             sidechain sulfur by covalent linkage to an
             acetamido group"

(ix) FEATURE:
         (A) NAME/KEY: Modified-site
         (B) LOCATION: 3
         (D) OTHER INFORMATION: /label= Acm
             /note= "This cysteine residue is blocked at the
             sidechain sulfur by covalent linkage to an
             acetamido group"

(xi) SEQUENCE DESCRIPTION: SEQ ID NO:29:

Cys Gly Cys Asn Asp Gly Asp Phe Glu Glu Ile Pro Glu Glu Tyr Leu
    1               5                   10                  15

Gln (2) INFORMATION FOR SEQ ID NO:30:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 3
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 6
        (D) OTHER INFORMATION: /label= D-Phe
            /note= "This residue is the D stereoisomer"

(xi) SEQUENCE DESCRIPTION: SEQ ID NO:30:

Cys Gly Cys Gly Gly Phe Pro Arg Pro Gly Gly Gly Gly Asn Gly Asp
    1              5                    10                 15

Phe Glu Glu Ile Pro Glu Glu Tyr Leu
             20             25

(2) INFORMATION FOR SEQ ID NO:31:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= ma
            /note= "The amino terminus is modified by covalent
            linkage to an mercaptoacetyl group."

(ix) FEATURE:
        (A) NAME/KEY: Modified-site
        (B) LOCATION: 5
        (D) OTHER INFORMATION: /label= D-Phe
            /note= "This residue is the D stereoisomer"

(xi) SEQUENCE DESCRIPTION: SEQ ID NO:31:

Gly Gly Gly Gly Phe Pro Arg Pro Gly Gly Gly Gly Asn Gly Asp Phe
    1              5                    10                 15

Glu Glu Ile Pro Glu Glu Tyr Leu
             20

(2) INFORMATION FOR SEQ ID NO:32:

(i) SEQUENCE CHARACTERISTICS:
        (A) LENGTH: 10 amino acids
        (B) TYPE: amino acid

```
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 3
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 6
            (D) OTHER INFORMATION: /label= D-Phe
                /note= "This residue is the D stereoisomer"

(ix) FEATURE:
            (A) NAME/KEY: Modified-site
            (B) LOCATION: 10
            (D) OTHER INFORMATION: /label= Amide
                /note= "The carboxyl terminus is modified to an
                amide"

(xi) SEQUENCE DESCRIPTION: SEQ ID NO:32:

Cys Gly Cys Gly Gly Phe Pro Arg Pro Gly
    1               5                   10

(2) INFORMATION FOR SEQ ID NO:33:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 18
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 20
            (D) OTHER INFORMATION: /label= Acm
                /note= "This cysteine residue is blocked at the
                sidechain sulfur atom by covalent linkage to an
                acetamido group"

(xi) SEQUENCE DESCRIPTION: SEQ ID NO:33:

Pro Ser Pro Ser Pro Ile His Pro Ala His His Lys Arg Asp Arg Arg
    1               5                   10                  15

Gln Cys Gly Cys
                20

(2) INFORMATION FOR SEQ ID NO:34:

(i) SEQUENCE CHARACTERISTICS:
            (A) LENGTH: 13 amino acids
            (B) TYPE: amino acid
            (D) TOPOLOGY: circular
```

```
    (ii) MOLECULE TYPE: peptide (ix) FEATURE:
         (A) NAME/KEY: Cross-links
         (B) LOCATION: 1...5
         (D) OTHER INFORMATION: /label= thioether
             /note= "The sulfur in the first cysteine is
             covalently linked to a [3-aminopropyl group; the
             sulfur of the second cysteine is linked to a
             [CH2CO] group to form a thioether, and said
             [CH2CO] group is further covalently linked
             to the N-terminal D-tyrosine to form an amide bond."

(ix) FEATURE:
         (A) NAME/KEY: Modified-site
         (B) LOCATION: 6
         (D) OTHER INFORMATION: /label= Apc
             /note= "The sulfur in the cysteine is covelantly
             linked to a [3-aminopropyl] group."

(ix) FEATURE:
         (A) NAME/KEY: Modified-site
         (B) LOCATION: 11
         (D) OTHER INFORMATION: /label= Acm
             /note= "This cysteine residue is blocked at the
             sidechain sulfur by covalent linkage to an
             acetamido group"

(ix) FEATURE:
         (A) NAME/KEY: Modified-site
         (B) LOCATION: 13
         (D) OTHER INFORMATION: /label= Acm
             /note= "This cysteine residue is blocked at the
             sidechain sulfur atom by covalent linkage to an
             acetamido group"

(ix) FEATURE:
         (A) NAME/KEY: Modified-site
         (B) LOCATION: 13
         (D) OTHER INFORMATION: /label= Amide
             /note= "The carboxyl terminus is modified to an
             amide"

(xi) SEQUENCE DESCRIPTION: SEQ ID NO:34:

Tyr Cys Gly Asp Cys Cys Gly Asp Phe Lys Cys Gly Cys
    1               5                   10

(2) INFORMATION FOR SEQ ID NO:35:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (ix) FEATURE:
         (A) NAME/KEY: Cross-links
         (B) LOCATION: 1...5
         (D) OTHER INFORMATION: /label= thioether
             /note= "The sulfur in the first cysteine is
             covalently linked to a [3-aminopropyl group; the
             sulfur of the second cysteine is linked to a
             [CH2CO] group to form a thioether, and said
             [CH2CO] group is further covalently linked
             to the N-terminal D-tyrosine to form an amide bond."

(ix) FEATURE:
         (A) NAME/KEY: Modified-site
         (B) LOCATION: 8
         (D) OTHER INFORMATION: /label= Acm
             /note= "This cysteine residue is blocked at the
             sidechain sulfur by covalent linkage to an
             acetamido group"

(ix) FEATURE:
         (A) NAME/KEY: Modified-site
         (B) LOCATION: 10
```

(D) OTHER INFORMATION: /label= Acm
                /note= "This cysteine residue is blocked at the
                sidechain sulfur atom by covalent linkage to an
                acetamido group"

(ix) FEATURE:
        (A) NAME/KEY: Modified-site
        (B) LOCATION: 10
        (D) OTHER INFORMATION: /label= Amide
            /note= "The carboxyl terminus is modified to an
            amide"

(xi) SEQUENCE DESCRIPTION: SEQ ID NO:35:

Tyr Cys Gly Asp Cys Lys Gly Cys Gly Cys
    1               5                   10

(2) INFORMATION FOR SEQ ID NO:36:

(i) SEQUENCE CHARACTERISTICS:
        (A) LENGTH: 13 amino acids
        (B) TYPE: amino acid
        (D) TOPOLOGY: circular (ii) MOLECULE TYPE: peptide (ix) FEATURE:
        (A) NAME/KEY: Cross-links
        (B) LOCATION: 1...5
        (D) OTHER INFORMATION: /label= thioether
            /note= "The sulfur in the first cysteine is
            covalently linked to a [3-aminopropyl group; the
            sulfur of the second cysteine is linked to a
            [CH2CO] group to form a thioether, and said
            [CH2CO] group is further covalently linked
            to the N-terminal D-tyrosine to form an amide bond."

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 11
        (D) OTHER INFORMATION: /label= Acm
            /note= "This cysteine residue is blocked at the
            sidechain sulfur atom by covalent linkage to an
            acetamido group"

(ix) FEATURE:
        (A) NAME/KEY: Modified-site
        (B) LOCATION: 13
        (D) OTHER INFORMATION: /label= Amide
            /note= "The carboxyl terminus is modified to an
            amide"

(xi) SEQUENCE DESCRIPTION: SEQ ID NO:36:

Tyr Cys Gly Asp Cys Gly Gly Cys Gly Cys Gly Gly Cys
    1               5                   10

(2) INFORMATION FOR SEQ ID NO:37:

(i) SEQUENCE CHARACTERISTICS:
        (A) LENGTH: 13 amino acids
        (B) TYPE: amino acid
        (D) TOPOLOGY: circular (ii) MOLECULE TYPE: peptide (ix) FEATURE:
        (A) NAME/KEY: Cross-links
        (B) LOCATION: 1...5
        (D) OTHER INFORMATION: /label= thioether

```
            /note= "The sulfur in the first cysteine is
            covalently linked to a [3-aminopropyl group; the
            sulfur of the second cysteine is linked to a
            [CH2CO] group to form a thioether, and said
            [CH2CO] group is further covalently linked
            to the N-terminal D-tyrosine to form an amide bond."

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 11
        (D) OTHER INFORMATION: /label= Acm
            /note= "This cysteine residue is blocked at the
            sidechain sulfur atom by covalent linkage to an
            acetamido group"

(ix) FEATURE:
        (A) NAME/KEY: Modified-site
        (B) LOCATION: 13
        (D) OTHER INFORMATION: /label= NES
            /note= "This cysteine residue is blocked at the
            sidechain sulfur atom by covalent linkage to an
            N-ethylsuccinimide group."

(ix) FEATURE:
        (A) NAME/KEY: Modified-site
        (B) LOCATION: 13
        (D) OTHER INFORMATION: /label= Amide
            /note= "The carboxyl terminus is modified to an
            amide"

(xi) SEQUENCE DESCRIPTION: SEQ ID NO:37:

Tyr Cys Gly Asp Cys Gly Gly Cys Gly Cys Gly Gly Cys
   1               5                   10

(2) INFORMATION FOR SEQ ID NO:38:

(i) SEQUENCE CHARACTERISTICS:
        (A) LENGTH: 17 amino acids
        (B) TYPE: amino acid
        (D) TOPOLOGY: circular (ii) MOLECULE TYPE: peptide (ix) FEATURE:
        (A) NAME/KEY: Cross-links
        (B) LOCATION: 1...5
        (D) OTHER INFORMATION: /label= thioether
            /note= "The sulfur in the first cysteine is
            covalently linked to a [3-aminopropyl group; the
            sulfur of the second cysteine is linked to a
            [CH2CO] group to form a thioether, and said
            [CH2CO] group is further covalently linked
            to the N-terminal D-tyrosine to form an amide bond."

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 11
        (D) OTHER INFORMATION: /label= Acm
            /note= "This cysteine residue is blocked at the
            sidechain sulfur atom by covalent linkage to an
            acetamido group"
```

(ix) FEATURE:
            (A) NAME/KEY: Modified-site
            (B) LOCATION: 13
            (D) OTHER INFORMATION: /label= D-Phe
                /note= "This residue is the D stereoisomer"

(ix) FEATURE:
            (A) NAME/KEY: Modified-site
            (B) LOCATION: 17
            (D) OTHER INFORMATION: /label= Amide
                /note= "The carboxyl terminus is modified to an
                amide"

(xi) SEQUENCE DESCRIPTION: SEQ ID NO:38:

Tyr Cys Gly Asp Cys Gly Gly Cys Gly Cys Gly Gly Phe Pro Arg Pro
       1               5                   10                  15

Gly (2) INFORMATION FOR SEQ ID NO:39:

(i) SEQUENCE CHARACTERISTICS:
            (A) LENGTH: 13 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1...5
            (D) OTHER INFORMATION: /label= thioether
                /note= "The sulfur in the first cysteine is
                covalently linked to a [3-aminopropyl group; the
                sulfur of the second cysteine is linked to a
                [CH2CO] group to form a thioether, and said
                [CH2CO] group is further covalently linked
                to the N-terminal D-tyrosine to form an amide bond."

(ix) FEATURE:
            (A) NAME/KEY: Modified-site
            (B) LOCATION: 8
            (D) OTHER INFORMATION: /label= Acm
                /note= "This cysteine residue is blocked at the
                sidechain sulfur by covalent linkage to an
                acetamido group"

(ix) FEATURE:
            (A) NAME/KEY: Modified-site
            (B) LOCATION: 11
            (D) OTHER INFORMATION: /label= Acm
                /note= "This cysteine residue is blocked at the
                sidechain sulfur atom by covalent linkage to an
                acetamido group"

(ix) FEATURE:
            (A) NAME/KEY: Modified-site
            (B) LOCATION: 13
            (D) OTHER INFORMATION: /label= Amide
                /note= "The carboxyl terminus is modified to an
                amide"

(xi) SEQUENCE DESCRIPTION: SEQ ID NO:39:

Tyr Cys Gly Asp Cys Lys Gly Cys Gly Cys Gly Gly Cys
       1               5                   10

(2) INFORMATION FOR SEQ ID NO:40:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (ix) FEATURE:

(A) NAME/KEY: Modified-site
          (B) LOCATION: 1
          (D) OTHER INFORMATION: /label= Pic
              /note= "The amino terminus is modified by covalent
              linkage to a picolinic acid group."

(ix) FEATURE:
          (A) NAME/KEY: Modified-site
          (B) LOCATION: 2
          (D) OTHER INFORMATION: /label= Acm
              /note= "This cysteine residue is blocked at the
              sidechain sulfur by covalent linkage to an
              acetamido group"

(ix) FEATURE:
          (A) NAME/KEY: Disulfide-bond
          (B) LOCATION: 5...11
          (D) OTHER INFORMATION: /label= disulfide
              /note= "The sidechain sulfur atoms of the cysteine
              residues are linked by a disulfide bond."

(ix) FEATURE:
          (A) NAME/KEY: Modified-site
          (B) LOCATION: 8
          (D) OTHER INFORMATION: /label= Apc
              /note= "The sidechain sulfur of the cysteine
              residue is covalently linked to a [3-aminopropyl]
              group forming a thioether"

(xi) SEQUENCE DESCRIPTION: SEQ ID NO:40:

Gly Cys Gly Gly Cys Asn Pro Cys Gly Asp Cys
    1               5                   10

(2) INFORMATION FOR SEQ ID NO:41:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= Acetyl
              /note= "The amino terminus is modified by covalent
              linkage to an acetyl group."

(ix) FEATURE:
          (A) NAME/KEY: Modified-site
          (B) LOCATION: 4
          (D) OTHER INFORMATION: /label= Amide
              /note= "The carboxyl terminus is modified to an
              amide"

(xi) SEQUENCE DESCRIPTION: SEQ ID NO:41:

Arg Gly Asp Cys
    1

(2) INFORMATION FOR SEQ ID NO:42:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (xi) SEQUENCE DESCRIPTION: SEQ ID NO:42:

Cys Arg Gly Asp Cys
    1               5

(2) INFORMATION FOR SEQ ID NO:43:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Apc
            /note= "The sidechain sulfur atom is covalently
            linked to a [3-aminopropyl] group to form a
            thioether"

(ix) FEATURE:
        (A) NAME/KEY: Modified-site
        (B) LOCATION: 7
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 9
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 13
        (D) OTHER INFORMATION: /label= Amide
            /note= "The carboxyl terminus is modified to an
            amide"

(xi) SEQUENCE DESCRIPTION: SEQ ID NO:43:

Gly Cys Gly Asp Val Lys Cys Gly Cys
 1               5

(2) INFORMATION FOR SEQ ID NO:44:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acetyl
            /note= "The amino terminus is modified by covalent
            linkage to an acetyl group."

(ix) FEATURE:
        (A) NAME/KEY: Modified-site
        (B) LOCATION: 10
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 12
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 12

5,925,331

69

-continued

```
            (D) OTHER INFORMATION: /label= Amide
                /note= "The carboxyl terminus is modified to an
                amide"

(xi) SEQUENCE DESCRIPTION: SEQ ID NO:44:

Arg Arg Ala Arg Gly Asp Asp Leu Asp Cys Gly Cys
     1               5                   10

(2) INFORMATION FOR SEQ ID NO:45:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= BAT
                /note= "The amino terminus is modified by covalent
                linkage to a BAT group."

(ix) FEATURE:
            (A) NAME/KEY: Modified-site
            (B) LOCATION: 2
            (D) OTHER INFORMATION: /label= Apc
                /note= "The sidechain sulfur atom is covalently
                linked to a [3-aminopropyl] group to form a
                thioether"

(ix) FEATURE:
            (A) NAME/KEY: Modified-site
            (B) LOCATION: 6
            (D) OTHER INFORMATION: /label= Apc
                /note= "The sidechain sulfur atom is covalently
                linked to a [3-aminopropyl] group to form a
                thioether"

(ix) FEATURE:
            (A) NAME/KEY: Modified-site
            (B) LOCATION: 10
            (D) OTHER INFORMATION: /label= Amide
                /note= "The carboxyl terminus is modified to an
                amide"

(xi) SEQUENCE DESCRIPTION: SEQ ID NO:45:

Gly Cys Gly Asp Val Cys Gly Asp Phe Lys
     1               5                   10

(2) INFORMATION FOR SEQ ID NO:46:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:46:

Cys Arg Ile Ala Arg Gly Asp Trp Asn Asp Asp Tyr Cys
     1               5                   10

(2) INFORMATION FOR SEQ ID NO:47:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (xi) SEQUENCE DESCRIPTION: SEQ ID NO:47:
```

```
        Cys Lys Phe Phe Ala Arg Thr Val Cys Arg Ile Ala Arg Gly Asp Trp
        1               5                   10                  15

Asn Asp Asp Tyr Cys Thr Gly Lys Ser Ser Asp Cys
                        20                  25
```

(2) INFORMATION FOR SEQ ID NO:48:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..5
        (D) OTHER INFORMATION: /label= thioether
            /note= "The sidechain sulfur of the C-terminal
            cysteine residue is covalently linked as an ether
            to the group [CH2CO], which group forms an amide
            bond with the N-terminal tyrosine residue"

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 10
        (D) OTHER INFORMATION: /label= Mob
            /note= "This cysteine residue is blocked at the
            sidechain sulfur atom by covalent linkage to an
            4-methoxybenzyl group."

(xi) SEQUENCE DESCRIPTION: SEQ ID NO:48:

```
        Tyr Ile Gly Ser Arg Cys Gly Cys Gly Cys
        1               5                   10
```

(2) INFORMATION FOR SEQ ID NO:49:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..5
        (D) OTHER INFORMATION: /label= thioether
            /note= "The sidechain sulfur of the C-terminal
            cysteine residue is covalently linked as an ether
            to the group [CH2CO], which group forms an amide
            bond with the N-terminal tyrosine residue"

(ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(ix) FEATURE:
        (A) NAME/KEY: Modified-site
        (B) LOCATION: 10
        (D) OTHER INFORMATION: /label= Amide
            /note= "The carboxyl terminus is modified to an
            amide"

(xi) SEQUENCE DESCRIPTION: SEQ ID NO:49:

Tyr Ile Gly Ser Arg Cys Gly Cys Gly Cys
    1               5                   10

(2) INFORMATION FOR SEQ ID NO:50:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:50:

Cys Tyr Gly Gln Gln His His Leu Gly Gly Ala Lys Gln Ala Gly Asp
    1               5                   10                  15

Val (2) INFORMATION FOR SEQ ID NO:51:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Pic
            /note= "The amino terminus is modified by covalent
            linkage to a picolinic acid group."

(ix) FEATURE:
        (A) NAME/KEY: Modified-site
        (B) LOCATION: 2
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:51:

Gly Cys Gly Gln Gln His His Leu Gly Gly Ala Lys Gln Ala Gly Asp
    1               5                   10                  15

Val (2) INFORMATION FOR SEQ ID NO:52:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Pic
            /note= "The amino terminus is modified by covalent
            linkage to a picolinic acid group."

(ix) FEATURE:
        (A) NAME/KEY: Modified-site
        (B) LOCATION: 2
        (D) OTHER INFORMATION: /label= Acm
            /note= "This cysteine residue is blocked at the
            sidechain sulfur by covalent linkage to an
            acetamido group"

-continued

```
   (ix) FEATURE:
        (A) NAME/KEY: Modified-site
        (B) LOCATION: 19
        (D) OTHER INFORMATION: /label= Amide
            /note= "The carboxyl terminus is modified to an
            amide"

(xi) SEQUENCE DESCRIPTION: SEQ ID NO:52:

Gly Cys Pro Ser Pro Ser Pro Ile His Pro Ala His His Lys Arg Asp
   1               5                  10                  15

Arg Arg Gln (2) INFORMATION FOR SEQ ID NO:53:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label= Acm
            /note= "This cysteine residue is blocked at the
            sidechain sulfur by covalent linkage to an
            acetamido group"

(xi) SEQUENCE DESCRIPTION: SEQ ID NO:53:

Gly Arg Gly Asp Phe Gly Gly Cys
   1               5
```

TECHNETIUM-99M LABELED PEPTIDES FOR THROMBUS IMAGING

This application is a cip of Ser. No. 08/886,752, filed May 21, 1992, now abandoned.

BACKGROUND OF THE INVENTION

1. Field of the Invention

This invention relates to radiodiagnostic reagents and methods for producing labeled radiodiagnostic agents. Specifically, the invention relates to reagents that can be labeled with technetium-99m (Tc-99m), methods and kits for making and radiolabeling such reagents, and methods for using such reagents to image sites of thrombus formation in a mammalian body.

2. Description of the Related Art

Thrombosis and thromboembolism, in particular deep vein thrombosis DVT) and pulmonary embolism (PE), are common clinical conditions that are associated with significant morbidity and mortality. It has been estimated that in the U.S. approximately 5 million patients experience one or more episodes of DVT per year and that over 500,000 cases of PE occur, resulting in 100,000 deaths (J. Seabold, Society of Nuclear Medicine Annual Meeting 1990). It has also been estimated that over 90% of all pulmonary emboli arise from DVT in the lower extremities. Foretunately, anticoagulant therapy can effectively treat these conditions, if applied early enough. However, such treatment is associated with risks (e.g. internal bleeding) that preclude unnecessary prophylactic application. More advanced techniques of thrombolytic intervention (such as the administration of recombinant tissue plasminogen activator or streptokinase) can be used in acute cases, but these techniques carry even greater risks. Moreover, effective clinical application of these techniques requires that the site of the offending thrombus be identified so as to monitor the effectiveness of treatment.

For these reasons, a rapid means of localizing thrombi in vivo, most preferably using non-invasive methods, is highly desirable. Methods currently utilized for the identification of thrombolytic sites are contrast venography and compression B-mode ultrasound; the choice of which technique is used depends on the expected location of the thrombus. However the former technique is invasive, and both techniques are uncomfortable for the patient. In addition, these methods are in many cases either unsuitable or yield inaccurate results.

In the field of nuclear medicine, certain pathological conditions are localized, or their extent is assessed, by detecting the distribution of small quantities of internally-administered, radioactively-labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. Tc-99m is a particularly preferred radionuclide because it emits gamma radiation at 140 keV, it has a physical half-life of 6 hours, and it is readily available on-site using a molybdenum-99/technetium-99m generator.

Radioimaging, specifically gamma scintigraphy, provides a non-invasive method for detecting the location of thrombi in vivo. A gamma-emitting radiotracer that binds specifically to a component of a thrombus in preference to other tissue when administered in vivo can provide an external scintigraphic image which defines the location of the thrombus-bound radiotracer and hence the thrombus.

There are several potential radiotracer targets in thrombi. Thrombi are constructs of blood cells, largely platelets, enmeshed in cross-linked fibrin protein. Venous thrombi are fibrin-rich, whereas arterial thrombi are platelet-rich. Fibrin and platelets are thus obvious targets for designing radiopharmaceutical for imaging thrombi, each having multiple possible target sites.

Activated platelets and fibrin have been used as targets in radioimaging thrombi because neither are normally found in circulating blood; circulating blood contains unactivated platelets and fibrinogen, a fibrin precursor. Thrombus formation involves the proteolytic conversion of fibrinogen to fibrin and the physiological conversion of unactivated platelets to an activated state. Since little fibrin circulates in the bloodstream (in contrast to its precursor, fibrinogen) and since most circulating platelets are unactivated, fibrin and activated platelets are excellent and specific targets for imaging thrombi because they will not be found to any substantial extent anywhere in vivo other than in a thrombus.

The use of radiolabeled fibrinogen and radiolabeled platelets for radioimaging has a number of disadvantages, however. Blood and background tissue clearance of radiolabeled fibrinogen and platelets are slow, which necessitates a long delay between injection and imaging. Also, as thrombi age radiolabeled platelets become less efficient imaging agents, although fibrin and platelets already in an existing thrombus remain targets even in aged thrombi.

Attempts to provide radiotracers for imaging thrombi are known in the prior art. These include autologous platelets, labeled with either $^{111}$In or $^{99m}$Tc (Tc-99m), and $^{123}$I- and $^{125}$I-labeled fibrinogen (the latter detected with a gamma scintillation probe as opposed to a gamma camera). In addition, other thrombus-associated components of the coagulation system, such as enzymes (e.g. thrombin), proenzymes and other factors may be useful as thrombus-associated targets for radiotracers. Additional radiolabeled compounds used to label thrombi include plasmin, plasminogen activators, heparin, fibronectin, fibrin Fragment $E_1$ and anti-fibrin and anti-platelet monoclonal antibodies [see Knight, 1990, Sem. Nucl. Med. 20: 52–67 for review].

Of the methods of radiolabeling thrombi known in the prior art, the methods that have shown the most promise are radiolabeled platelets, radiolabeled antibodies and radiolabeled fibrin Fragment $E_1$. All of these have serious drawbacks with regard to their routine use.

The use of radiolabeled autologous platelets to image thrombi requires that autologous blood be drawn, the platelets then separated and radiolabeled under sterile conditions (in addition, radiolabeling must be performed so as to avoid activating the platelets), and the radiolabeled platelets then readministered to the patient. Such radiolabeled platelets have a long circulating time, resulting in poor target to non-target ratios at early times, and thereby requiring that radioimaging be performed only after a delay of 24 to 72 hours. Moreover, aged thrombi are poorly visualized since such thrombi do not efficiently incorporate fresh platelets.

Radiolabeled antifibrin and antiplatelet monoclonal antibodies have also been used in the prior art (typically to image DVT). The disadvantage to using such reagents is that antibodies (and even antibody fragments) have slow blood and general tissue clearance characteristics and require a delay of at least several hours for optimum imaging. En addition, immunological reagents have the capacity to induce an immune response in the patient. Further, such reagents must be prepared from mammalian cell lines (hybridomas) and thus carry the risk of contamination by infectious human viruses.

Methods of using radiolabeled proteins and proteolytic fragments thereof for imaging thrombi have been described in the prior art. For example, Fragment $E_1$ is a proteolytic fragment of fibrin that is derived from coagulated, cross-linked fibrin. It has been labeled with 123I and Tc-99m to provide high quality images in humans.

Olexa et al., 1982, European Patent Application No. 823017009 disclose pharmaceutically acceptable radiolabeled prpteolytic fragments selected from Fragment $E_1$ isolated from cross-linked fibrin, Fragment $E_2$ isolated from cross-linked fibrin, and proteolytic fragments having amino acid sequences intermediate between Fragments $E_1$ and $E_2$. Unfortunately, these protein fragments must be laboriously prepared from human fibrinogen, making them unsuitable for routine manufacture.

Headley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Sobel, 1989, PCT/US89/02656 discloses a method to locate the position of one or more thrombi in an animal using radiolabeled, enzymatically inactive tissue plasminogen activator.

Peptides having the ability to bind to thrombi are known in the prior art.

Ruoslahti & Pinerschbacher, U.S. Pat. No. 4,578,079 describe peptides of sequence X—Arg—Gly—Asp—R—Y, wherein X and Y are either H or an amino acid, and R is Thr or Cys, the peptides capable of binding to thrombi in vivo.

Ruoslahti & Pierschbacher, U.S. Pat. No. 4,792,525 describe peptides of sequence Arg—Gly—Asp—X, wherein X is Ser, Thr or Cys, the peptides capable of binding to thrombi in vivo.

Klein et al., 1992, U.S. Pat. No. 5,086,069 disclose guanine derivatives that bind to the GPIIb/IIIa receptor, found on the cell surface of activated platelets.

Pierschbacher et al., 1989, PCT/US88/04403 disclose conformationally-restricted RGD-containing peptides for inhibiting cell attachment to a substratum.

Hawiger et al., 1989, PCT/US89/01742 relates to peptides comprising sequences for two binding sites of a protein.

Nutt et al., 1990, Europe Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Pierschbacher et al., 1991, PCT/US91/02356 disclose cyclic peptides that are fibrinogen receptor antagonists.

Egbertson et al., 1992, European Patent Application 0478328A1 disclose tyrosine derivatives that bind with high affinity to the GPIIb/IIIa receptor.

Ojima et al., 1992, 204th Meeting, Amer. Chem. Soc. Abst. 44 disclose synthetic multimeric RDGF peptides useful in inhibiting platelet aggregation.

Hartman et al., 1992, J. Med. Chem. 35: 4640–4642 describe tyrosine derivatives that have a high affinity for the GPIIb/IIIa receptor.

Radiolabeled peptides useful for radioimaging thrombi have been reported in the prior art.

Ranby et al., 1988, PCT/US88/02276 disclose a method for detecting fibrin deposits in an animal comprising covalently binding a radiolabeled compound to fibrin.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Rodwell et al., 1991, PCT/US91/03116 disclose conjugates of "molecular recognition units" with "effector domains".

Maraganore et al., 1991, PCT/US90/04642 disclose a radiolabeled thrombus inhibitor comprising (a) a inhibitor moiety; (b) a linker moiety; and (c) an "anion binding exosite (ABE)" binding site moiety.

The use of chelating agents for radiolabeling polypeptides, and methods for labeling peptides and polypeptides with Tc-99m are known in the prior art and are disclosed in co-pending U.S. patent applications Ser. Nos. 07/653,012, 07/807,062, 07/871,282, 07/886,752, 07/893,981, 07/955,466, 08/019,864 and 08/044,825, and PCT International Applications PCT/US92/00757, PCT/US92/10716, PCT/US93/02320 and PCT/US93/, which are hereby incorporated by reference.

There remains a need for small (to enhance blood and background tissue clearance), synthetic (to make routine manufacture practicable and to ease regulatory acceptance) molecules radiolabeled with Tc-99m for use in imaging thrombi in vivo. Small synthetic peptides radiolabeled with Tc-99m that bind specifically to components of thrombi fulfill this need and are provided by this invention.

SUMMARY OF THE INVENTION

The present invention provides radioactively-labeled reagents that are scintigraphic imaging agents. Specifically, the invention provides reagents for preparing thrombus imaging agents that are radiolabeled with technetium-99m (Tc-99m). The reagents of the invention are each comprised of a specific binding compound, including but not limited to peptides, that binds specifically to a thrombus in vivo, and that is covalently linked to a radiolabel-binding moiety.

In preferred embodiments, the invention provides reagents wherein the 10 specific binding compounds are linear or cyclic peptides having an amino acid sequence of 4 to 200 amino acids.

It is of distinct commercial advantage to use small compounds, preferably having a molecular weight of less than about 10,000 daltons. Such small compounds can be readily manufactured. Moreover, they are likely not to be immunogenic and to clear rapidly from the vasculature, thus allowing for better and more rapid imaging of thrombi. In contrast, larger molecules such as antibodies of fragments thereof, or other biologically-derived peptides larger than 10,000 daltons, are costly to manufacture, and are likely to be immunogenic and clear more slowly from the bloodstream, thereby interfering with rapid diagnoses of thrombi in vivo.

One aspect of the invention provides a reagent for preparing a thrombus imaging agent that is capable of being radiolabeled for imaging thrombi within a mammalian body, comprising a specific binding compound that specifically binds to at least one component of a thrombus, covalently linked to a Tc-99m binding moiety of formula:

$$C(pgp)^s\text{-}(aa)\text{-}C(pgp)^s$$

wherein $C(pgp)^s$ is a protected cysteine and (aa) is an amino acid. In a preferred embodiment, the amino acid is glycine.

In another embodiment, the invention provides a reagent for preparing a thrombus imaging agent that is capable of being radiolabeled for imaging thrombi within a mammalian body, comprising a specific binding compound that specifically binds to at least one component of a thrombus, covalently linked to a Tc-99m binding moiety of formula:

$$A\text{—}CZ(B)\text{—}[C(R^1R^2)]_n\text{—}X$$

wherein A is H, HOOC, $H_2NOC$, (peptide)—NHOC, (peptide)—OOC or $R^4$; B is H, SH or —$NHR^3$, —$N(R^3)$-(peptide) or $R^4$; Z is H or $R^4$; X is SH or —$NHR^3$, —$N(R^3)$—(peptide) or $R^4$; $R^1$, $R^2$, $R^3$ and $R^4$ are independently H or straight or branched chain or cyclic lower alkyl; n is 0, 1 or 2; and: (1) where B is —$NHR^3$ or —$N(R^3)$-(peptide), X is SH and n is 1 or 2; (2) where X is —$NHR^3$ or —$N(R^3)$-(peptide), B is SH and n is 1 or 2; (3) where B is H or $R^4$, A is HOOC, $H_2NOC$, (peptide)—NHOC, (peptide)—OOC, X is SH and n is 0 or 1; (4) where A is H or $R^4$, then where B is SH, X is —$NHR^3$ or —$N(R^3)$-(peptide) and where X is SH, B is —$NHR^3$ or —$N(R^3)$-(peptide); (5) where X is H or $R^4$, A is HOOC, $H_2NOC$, (peptide)—NHOC, (peptide)—OOC and B is SH; (6) where Z is methyl, X is methyl, A is HOOC, $H_2NOC$, (peptide)—NHOC, (peptide)—OOC and B is SH and n is 0; and (7) where Z is SH and X is SH, n is not 0; and wherein the thiol moiety is in the reduced form.

In another embodiment, the invention provides a reagent for preparing a thrombus imaging agent that is capable of being radiolabeled for imaging thrombi within a mammalian body, comprising a specific binding compound that specifically binds to at least one component of a thrombus, covalently linked to a radiolabel binding moiety of formula:

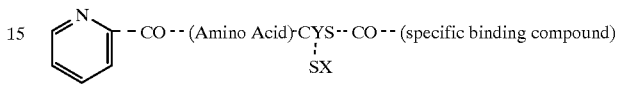

[for purposes of this invention, radiolabel-binding moieties having this structure will be referred to as picolinic acid (Pic)-based moieties] or

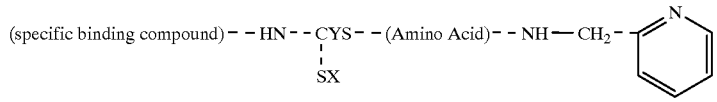

[for purposes of this invention, radiolabel-binding moieties having this structure will be referred to as picolylamine (Pica)-based moieties]; wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the specific binding compound is covalently linked to the radiolabel-binding moiety via an amino acid, most preferably glycine.

Yet another embodiment of the invention provides a reagent for preparing a thrombus imaging agent that is capable of being radiolabeled for imaging thrombi within a mammalian body, comprising a specific binding compound that specifically binds to at least one component of a thrombus, covalently linked to a radiolabel-binding moiety that is a bisamino bisthiol radiolabel binding moiety. The bisamino bisthiol moiety in this embodiment of the invention has a formula selected from the group consisting of:

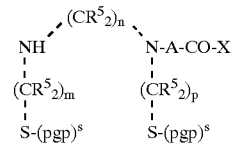

wherein each $R^5$ can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is a specific binding compound, preferably a peptide; and

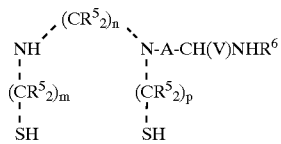

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-peptide; $R^6$ is H or peptide; provided that when V is H, $R^6$ is peptide and when $R^6$ is H, V is peptide. [For purposes of this invention, radiolabel-binding moieties having these structures will be referred to as "BAT" moieties]. In a preferred embodiment, the specific binding compound of the reagent is covalently linked to the radiolabel-binding moiety via an amino acid, most preferably glycine.

In preferred embodiments of the aforementioned aspects of this invention, the specific binding compound is a peptide is comprised of between 4 and 100 amino acids. The most preferred embodiment of the radiolabel is technetium-99m.

The reagents of the invention may be formed wherein the specific binding compounds or the radiolabel-binding moieties are covalently linked to a polyvalent linking moiety. Polyvalent linking moieties of the invention are comprised of at least 2 identical linker functional groups capable of covalently bonding to specific binding compounds or radiolabel-binding moieties. Preferred linker functional groups are primary or secondary amines, hydroxyl groups, carboxylic acid groups or thiol-reactive groups. In preferred embodiments, the polyvalent linking moieties are comprised of bis-succinimdylmethylether (BSME), 4-(2,2-dimethylacetyl)benzoic acid (DMAB), tris(succinimidylethyl)amine (TSEA), N-[2-(N_,N_-bis(2-succinimidoethyl) aminoethyl)]—$N^6$,$N^9$-bis(2-methyl-2-mercaptopropyl)-6,9-diazanonanamide (BAT-BS), 4-(O—$CH_2CO$—Gly—Gly—Cys.amide)acetophenone (ETAC) and bis-succinimidohexane (BSH).

The invention also provides thrombus imaging agents for imaging a thrombus within a mammalian body comprising a specific binding peptide having an amino acid sequence of 4 to 100 amino acids and a technetium-99m binding moiety covalently linked to the specific binding peptide, wherein the peptide is selected from the group consisting of linear and cyclic peptides that are ligands for a GPIIb/IIIa receptor and do not comprise the amino acid sequence (arginine-glycine-aspartate), peptides that are ligands for a polymerization site of fibrin, and cyclic peptides comprising the amino acid sequence (arginine-glycine-aspartate). In a preferred embodiment, the amino acid sequence of peptides that are ligands for a polymerization site of fibrin comprise multiple copies of the sequence (glycyl-prolyl-arginyl-prolyl).

The invention also comprises scintigraphic imaging agents that are complexes of the reagents of the invention with Tc-99m and methods for radiolabeling the reagents of the invention with Tc-99m. Radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

The invention also provides kits for preparing scintigraphic imaging agents that are the reagents of the invention radiolabeled with Tc-99m. Kits for labeling the reagents of the invention with Tc-99m are comprised of a sealed vial containing a predetermined quantity of a reagent of the invention or mixtures thereof and a sufficient amount of reducing agent to label the reagent with Tc-99m.

This invention provides methods for preparing reagents of the invention by chemical synthesis in vitro. In preferred embodiments, peptides are synthesized by solid phase peptide synthesis.

This invention provides methods for using scintigraphic imaging agents that are Tc-99m labeled reagents for imaging a thrombus within a mammalian body by obtaining in vivo gamma scintigraphic images. These methods comprise administering an effective diagnostic amount of Tc-99m labeled reagents of the invention and detecting the gamma radiation emitted by the Tc-99m label localized at the thrombus site within the mammalian body.

Specific preferred embodiments of the present invention will become evident from the following more detailed description of certain preferred embodiments and the claims.

DETAILED DESCRIPTION OF THE INVENTION

Figure 1:
FIG. 1 shows scintigraphic images showing the location of venous thrombi in vivo detected using Tc-99m labeled peptide as disclosed in Example 4.

The present invention provides reagents, including peptide reagents, for preparing radiolabeled thrombus imaging agents for imaging a thrombus within a mammalian body. The reagents provided by the invention comprise a radiolabel binding moiety covalently linked to a specific binding compound that is capable of binding to at least one component of a thrombus. For purposes of the invention, the term thrombus imaging reagent will refer to embodiments of the invention comprising a specific binding compound covalently linked to a radiolabel binding moiety and radiolabeled, preferably with Tc-99m, $^{111}$In or $^{68}$Ga, most preferably with Tc-99m.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Another advantage of the present invention is that none of the preferred radionuclides are toxic, in contrast to other radionuclides known in the art (for example, $^{125}$I).

In the Tc-99m binding moieties and compounds covalently linked to such moieties that contain a thiol covalently linked to a thiol protecting groups [$(pgp)^5$] provided by the invention, the thiol-protecting groups may be the same or different and may be but are not limited to:

—$CH_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—$CH_2$—(4-methoxyphenyl);

—CH—(4-pyridyl)(phenyl)$_2$;

—C($CH_3$)$_3$-9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$-phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D- amino acids, naturally occurring and otherwise. Reagents comprising specific-binding peptides provided by the invention include but are not limited to the following (the amino acids in the following peptides are L-amino acids except where otherwise indicated):

Ligands for the GPIIb/IIIa Receptor

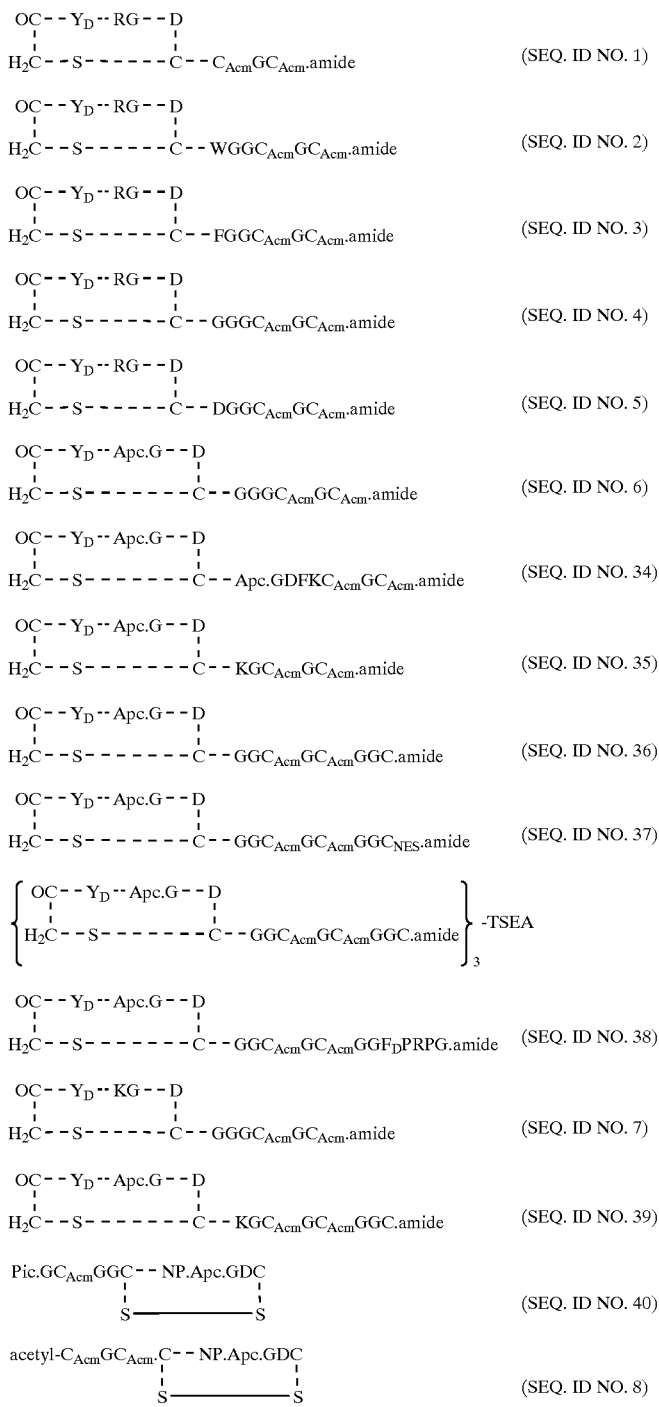

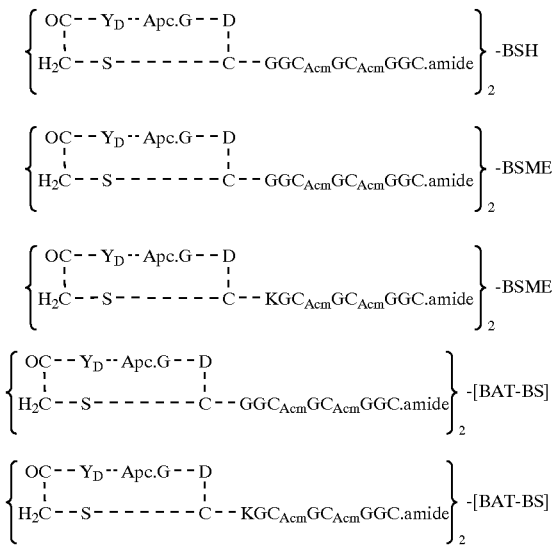

$C_{Acm}GC_{Acm}$GGRGDS (SEQ ID NO. 9)
$C_{Acm}GC_{Acm}$GGRGDGGRGDS (SEQ ID NO. 10)
$C_{Acm}GC_{Acm}$GGRGDGGRGDGGRGDS (SEQ ID NO. 11)
CKRARGDDMDDYC (SEQ ID NO. 12)
$C_{Acm}GC_{Acm}$RRRRRRRRRGDV (SEQ ID NO. 13)
GRGDVK$C_{Acm}GC_{Acm}$.amide (SEQ ID NO. 14)
GRGDV$C_{Acm}GC_{Acm}$.amide (SEQ ID NO. 15)
GRGDVRGDFK$C_{Acm}GC_{Acm}$.amide (SEQ ID NO. 16)
GRGDVRGDF$C_{Acm}GC_{Acm}$.amide (SEQ ID NO. 17)
mmp-GGGRGDF (SEQ ID NO. 18)
acetyl—CNP.Apc.GDC (SEQ ID NO. 19)
acetyl—RGDC.amide (SEQ ID NO. 41)
CRGDC (SEQ ID NO. 42)
GRGDFGG$C_{Acm}$ (SEQ ID NO. 53)
ma$_{Bz}$—GGRGDF (SEQ ID NO. 25)
$C_{Acm}$GGGRGDF (SEQ ID NO. 22)
GRGDGGGC (SEQ ID NO. 23)
GRGDGG$C_{Acm}$ (SEQ ID NO. 20)
ma—GGRGDF (SEQ ID NO. 21)
ma$_{Acm}$—GGGRGDF (SEQ ID NO. 24)
ma—RGDF (SEQ ID NO. 25)
ma—RGD (SEQ ID NO. 27)
acetyl—G.Apc.GDV.Apc.GDFK$C_{Acm}GC_{Acm}$.amide
G.Apc.GDV.Apc.GDFK$C_{Acm}GC_{Acm}$.amide
G.Apc.GDVK$C_{Acm}GC_{Acm}$.amide (SEQ ID NO. 43)
acetyl—RRARGDDLD$C_{Acm}GC_{Acm}$amide (SEQ ID NO. 44)
(C$C_{Acm}GC_{Acm}$GGRGDS)$_3$—TSEA
[Pic.S$C_{Acm}$SYNRGDSTC.amide]$_3$—TSEA
[BAT].Hly.GDP.Hly.GDF.amide (SEQ ID NO. 28)
[BAT]G.Apc.GDV.Apc.GDFK.amide (SEQ ID NO. 45)
CRIARGDWNDDYC (SEQ ID NO. 46)
CKFFARTVCRIARGDWNDDYCTGKSSDC (SEQ ID NO. 47)
Thrombin Ligands $C_{Acm}GC_{Acm}$NDGDFEEIPEEYLQ (SEQ ID NO. 29)
$C_{Acm}GC_{Acm}$GGF$_D$PRPGGGGNGDFEEIPEEYL (SEQ ID NO. 30)
ma—GGGGF$_D$PRPGGGGNGDFEEIPEEYL (SEQ ID NO. 31)
$C_{Acm}GC_{Acm}$GGF$_D$PRPGamide (SEQ ID NO. 32)
(acetyl—F$_D$PRPG)$_2$KGGGC.amide
Ligands for the Polymerization Site of Fibrin
[(GPRP)$_2$K]$_2$K$C_{Acm}GC_{Acm}$.amide
(GPRVVERHQSA)$_2$K$C_{Acm}GC_{Acm}$.amide
(GPRP$C_{Acm}GC_{Acm}$C)$_3$—TSEA
[GPRPPPGG$C_{Acm}GC_{Acm}$GGC]$_3$—TSEA
Derivatives of Laminin

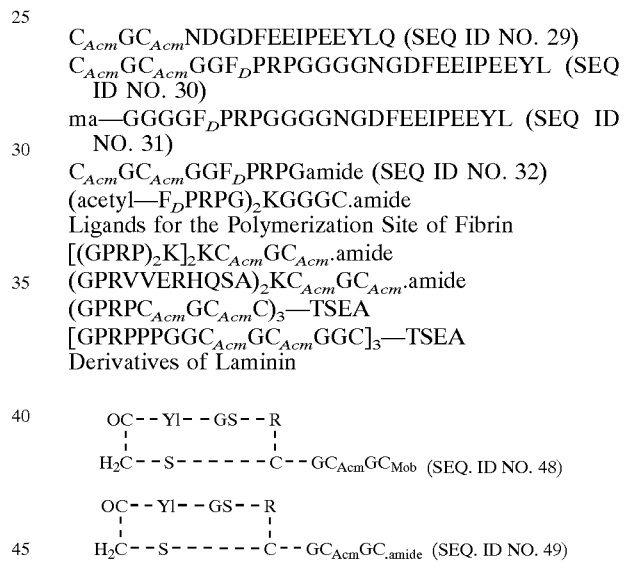

Ligands for Fibrinogen
CYGQQHHLGGAKQAGDV (SEQ ID NO. 50)
Pic.G$C_{Acm}$GQQHHLGGAKQAGDV (SEQ ID NO. 51)
Derivatives of GPIIb/IIIa
Pic.G$C_{Acm}$PSPSPIHPAHHKRDRRQ.amide (SEQ ID NO. 52)
PSPSPIHPAHHKRDRRQ$C_{Acm}GC_{Acm}$.amide (SEQ ID NO. 33)

(Single-letter abbreviations for amino acids can be found in G. Zubay, *Biochemistry* (2d. ed.), 1988 (MacMillen Publishing: New York) p.33; other abbreviations are as in the Legend to Table I). This list of reagents provided by the invention is illustrative and not intended to be limiting or exclusive, and it will be understood by those with skill in the art that reagents comprising combinations of the peptides diclosed herein or their equivalents may be covalently linked to any of the chelating moieties of the invention and be within its scope, including combinations of such peptides and chelating moieties comprising linking groups as disclosed herein.

In embodiments of the invention comprising peptides having an amino acid sequence that encode the platelet GPIIb/IIIa receptor, each said reagent is capable of inhibiting human platelet aggregation in platelet-rich plasma by 50% when present at a concentration of no more than 0.3 μM.

Specific-binding peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid [(Pic—); e.g., Pic—Gly—Cys(protecting group)-], the radiolabel-binding moiety can be synthesized as the last (i.e., amino-terminal) residue in the synthesis. In addition, the picolinic acid-containing radiolabel-binding moiety may be covalently linked to the E-amino group of lysine to give, for example, aN(Fmoc)—Lys—EN[Pic—Gly—Cys (protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-CYS(protecting group)—Gly—Pica] can be prepared during peptide synthesis by including the sequence [—Cys(protecting group)—Gly—] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic—Gly—Cys— and —Cys—Gly—Pica chelators are provided in the Examples hereinbelow. This invention provides for the incorporation of these chelators into virtually any peptide capable of specifically binding to a thrombus in vivo, resulting in a radiolabeled peptide having Tc-99m held as neutral complex.

This invention also provides specific-binding small synthetic peptides which incorporate bisamine bisthiol (BAT) chelators which may be labeled with Tc-99m. This invention provides for the incorporation of these chelators into virtually any peptide capable of specifically binding to a thrombus in vivo, resulting in a radiolabeled peptide having Tc-99m held as neutral complex. Examples of small synthetic peptide reagents containing BAT chelators as radiolabel-binding moiety is provided in the Examples hereinbelow.

In forming a complex of radioactive technetium-99m with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled reagents is provided. An appropriate amount of the reagent is introduced into a vial containing a reducing agent, such as stannous chloride, in an amount sufficient to label the reagent with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus imaging reagents according to the present invention may be prepared by the addition of an appropriate amount of Tc-99m or Tc-99m complex into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The thrombus imaging reagents provided by the present invention can be used for visualizing thrombi in a mammalian body when Tc-99m labeled. In accordance with this invention, the Tc-99m labeled reagents are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the radiolabeled reagent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzotriazol-1-yl)-1,1,3,3-tetramethyluronium hexafluorophosphate/ hydroxybenzotriazole (HBTU/HOBT), and using p-hydroxymethylphenoxy-methylpolystyrene (HMP) resin for carboxyl-terminus acids or Rink amide resin for carboxyl-terminus amides. Resin-bound products were routinely cleaved using a solution comprised of trifluoroacetic acid, water, thioanisole (if an arginine residue comprises the peptide), ethanedithiol, and triethylsilane, prepared in ratios of 100:5:5:2.5:2 for 0.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/ diisopropylethylamine in NMP. Where appropriate, 2-haloacetylated peptides were cyclized by stirring an 0.1–1.0 mg/mL solution in phosphate or bicarbonate buffer (pH 8) containing 0.5–1.0 mM EDTA for 4–48 hours, followed by acidification with acetic acid, lyophilization and HPLC purification. Where appropriate, Cys—Cys disulfide bond cyclizations were performed by treating the precursor cysteine-free thiol peptides at 0.1 mg/mL in pH 7 buffer with aliquots of 0.006M $K_3Fe(CN)_6$ until a stable yellow color persisted. The excess oxidant was reduced with excess cysteine, the mixture lyophilized and then purified by HPLC.

Where appropriate the "Pic" group was introduced by using picolinic acid as the last residue in peptide synthesis. Where appropriate the "Pica" group was introduced by conjugating picolylamine to a precursor peptide using diisopropylcarbodiimide and N-hydroxysuccinimide. Where appropriate BAT ligands were introduced either by using the appropriate BAT acid as the last residue to be coupled during SPPS or by treating the N-terminus free amino peptide bound to the resin with BAT acid/diisopropylcarbodiimide/ N-hydroxysuccinimide in NMP. Where appropriate, [BAM] was conjugated to the peptide by first activating the peptide carboxylate with a mixture of diisopropylcarbodiimide/N-hydroxysuccinimide or HBTU/HOBt in DMF, NMP or $CH_2Cl_2$, followed by coupling in the presence of diisopropylethylamine; after coupling, the conjugate was deprotected as described above.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) pre-dissolved in acetonitrile at room temperature for approximately 1–18 hours. The solution was concentrated and the product was purified by HPLC. Where appropriate, BSH adducts were prepared by using bis-maleimidohexane in place of BMME.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/acetonitrile or THF) with 0.33 molar equivalents of TMEA (tris(2-maleimidoethyl)amine; see co-pending U.S. patent application Ser. No. 07/955,466, incorporated by reference) pre-dissolved in acetonitrile or DMF, with or without I molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-[2-(N',N'-bis(2-maleimidoethyl)aminoethyl)]-$N^9$-(t-butoxycarbonyl)-$N^6$,$N^9$-bis(2-methyl-2-triphenylmethylthiopropyl)-6,9-diazanonanamide; see co-pending U.S. patent application Ser. No. 08/044,825, incorporated by reference) pre-dissolved in acetonitrile or THF, at room temperature for approximately 1–18 h. The solution was then evaporated to dryness and [BAT-BS]-peptide conjugates deprotected by treatment with 10 mL TFA and 0.2 mL triethylsilane for 1 h. The solution was concentrated, the product adducts precipitated with ether, and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m 0.1 mg of a peptide reagent prepared as in Example 2 was dissolved in 0.1 mL of water, or 50:50 ethanol:water, or phosphate-buffered saline (PBS), or 50 mM potassium phosphate buffer (pH=5, 6 or 7.4). Tc-99m gluceptate was prepared by reconstituting a Glucoscan vial (E. I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature or at 100° C. for 15–30 min and then filtered through a 0.2 μm filter.

The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides | FABMS MH$^+$ | Radiochemical Yield (%)* | HPLC R$_T$ (min)** |
|---|---|---|---|
| CH$_2$CO.Y$_D$RGDCC$_{Acm}$GC$_{Acm}$amide | 1057 | 97$^2$ | 10.0, 10.4, 10.6$^2$ |
| CH$_2$CO.Y$_D$RGDCWGGC$_{Acm}$GC$_{Acm}$amide | 1357 | 100$^4$ | 15.9, 16.4$^2$ |
| CH$_2$CO.Y$_D$RGDCFGGC$_{Acm}$GC$_{Acm}$amide | 1318 | 97$^4$ | 15.9, 16.3$^2$ |
| CH$_2$CO.Y$_D$RGDCGGGC$_{Acm}$GC$_{Acm}$amide | 1310 | 99$^2$ | 11.8$^2$ |
| CH$_2$CO.Y$_D$RGDCGGC$_{Acm}$GC$_{Acm}$amide | 1171 | 99$^2$ | 13.5$^2$ |
| CH$_2$CO.Y$_D$.Apc.GDCGGGC$_{Acm}$GC$_{Acm}$amide | 1233 | 100$^4$ | 17.1, 18.1$^2$ |
| CH$_2$CO.Y$_D$KGDCGGGC$_{Acm}$GC$_{Acm}$amide | 1200 | 96$^4$ | 15.8, 16.1$^2$ |
| Pic.GC$_{Acm}$GGCNP.Apc.GDC | 1217 | 70$^2$ | 6.6–13.7$^2$ |
| Ac.C$_{Acm}$GC$_{Acm}$GGCNP.Apc.GDC | 1327 | 98$^2$ | 13.0–15.5$^2$ |
| Ac.CNP.Apc.GDC | 810 | 99$^1$ | 12.9$^2$ |
| C$_{Acm}$GC$_{Acm}$GGRGDS | 953 | 100$^2$ | 8.6$^1$ |
| C$_{Acm}$GC$_{Acm}$GGRGDGGRGDS | 1396 | 100$^1$ | 12.6$^1$ |
| C$_{Acm}$GC$_{Acm}$GGRGDGGRGDGGRGDS | 1838 | 100$^2$ | 10.0, 10.8$^1$ |
| C$_{Acm}$GC$_{Acm}$RRRRRRRRGDV | 2100 | 100$^2$ | 2.4$^{3***}$ |
| GRGDVKC$_{Acm}$GC$_{Acm}$amide | 1036 | 100$^2$ | 15.7$^2$ |
| GRGDVC$_{Acm}$GC$_{Acm}$amide | 907 | 100$^2$ | 16.1$^2$ |
| GRGDVRGDFKC$_{Acm}$GC$_{Acm}$amide | 1510 | 97$^2$ | 16.2, 16.8$^2$ |
| GRGDVRGDFC$_{Acm}$GC$_{Acm}$amide | 1382 | 94$^2$ | 16.4$^2$ |
| (GPRVVERHQSA)$_2$K | 2986 | 99$^4$ | 16.0$^2$ |
| CRGDC | 553 | 100$^3$ | 16.7$^2$ |
| GRGDGGC | 769 | 98$^1$ | 13.0, 13.6, 14,7$^2$ |
| CH$_2$CO.YIGSRCGC$_{Acm}$GC$_{Mob}$ | 1249 | 96$^2$ | 18.0$^1$ |
| CYGQQHHLGGAKQAGDV | N.D. | 97$^2$ | 23.8$^3$ |
| acetyl-RRARGDDLDC$_{Acm}$GC$_{Acm}$.amide | 1520 | 98$^2$ | 10.8$^2$ |
| Pic.GC$_{Acm}$GQQHHLGGAKQAGDV | 1838 | 48$^2$ | 14.8$^2$ |
| maGGRGDF | 739 | 98$^1$ | 13.8–14.7$^2$ |
| mmpGGGRGDF | 767 | 100$^3$ | 18.4, 19.3$^2$ |
| GRGDGGGGC | 735 | 100$^3$ | 14.9, 15.1, 15.4$^3$ |
| maRGD | 421 | 97$^3$ | 16.1, 16.9, 17.7$^2$ |
| maRGDF | 568 | 94$^3$ | 18.1, 18.7$^2$ |
| CKRARGDDMDDYC | 1548 | 97$^3$ | 16.7$^2$ |
| (Pic.SC$_{Acm}$SYNRGDSTC)$_3$—TSEA | 4489 | 99$^2$ | 10.4, 11.2$^2$ |
| C$_{Acm}$GC$_{Acm}$NDGDFEEIPEEYLQ | 2103 | 100$^2$ | 2.5$^{1****}$ |
| C$_{Acm}$GC$_{Acm}$GGF$_D$PRPGGGGNGDFEEIPEEYL | 2699 | 99$^2$ | 14.5$^3$ |
| maGGGF$_D$PRPGGGGNGDFEEIPEEYL | 2426 | 95$^2$ | 17.4$^2$ |
| C$_{Acm}$GC$_{Acm}$GGF$_D$PRPGamide | 1092 | 100$^5$ | 9.6$^2$ |
| (GPRPC$_{Acm}$GC$_{Acm}$C)$_3$—TSEA | 3189 | 93$^2$ | 10.0$^2$ |
| [(GPRP)$_2$K]$_2$KC$_{Acm}$GC$_{Acm}$amide | 2437 | 100$^4$ | 16.3$^2$ |
| (CC$_{Acm}$GC$_{Acm}$GGRDGS)$_3$—TSEA | N.D. | 81$^2$ | 9.9–11.1$^2$ |
| PSPSPIHPAHHKRDRRQC$_{Acm}$GD$_{Acm}$.amide | 2421 | 94$^2$ | 13.4$^2$ |
| (acetyl-F$_D$PRPG)$_2$KGGGC.amide | 1613 | 98$^3$ | 17.4$^2$ |
| CH$_2$CO.Y$_D$Apc.GDCGGC$_{Acm}$GC$_{Acm}$GGF$_D$PRPG.amide | 1845 | 90$^4$ | 16.6, 16.9$^2$ |
| CH$_2$CO.Y$_D$.Apc.GDCGGC$_{Acm}$GC$_{Acm}$.GGCamide | 1392 | 99$^3$ | 11.7$^4$ |
| acetyl-G.Apc.GDV.Apc.GDFKC$_{Acm}$GC$_{Acm}$.amide | 1561 | 100$^4$ | 9.3, 9.8$^2$ |
| [BAT].Hly.GDP.Hly.GDF.amide | 1209 | 100$^3$ | 10.8$^2$ |
| (CH$_2$CO.Y$_D$Apc.GDCGGC$_{Acm}$GC$_{Acm}$GGC.amide)$_2$—BSME | 3020$^a$ | 98$^4$ | 9.3$^2$ |
| CH$_2$CO.Y$_D$Apc.GDCKGC$_{Acm}$GC$_{Acm}$.amide | 1282 | 99$^4$ | 15.8, 16.1$^2$ |
| CH$_2$CO.Y$_D$.Apc.GDC.Apc.GDFKC$_{Acm}$GC$_{Acm}$.amide | 1669 | 99$^4$ | 16.2, 16.6$^2$ |
| G.Apc.GDV.Apc.GDFKC$_{Acm}$GC$_{Acm}$.amide | 1519 | 99$^4$ | 9.3, 9.8$^2$ |
| G.Apc.GDFKC$_{Acm}$GC$_{Acm}$.amide | 1040 | 100$^4$ | 9.4$^2$ |
| (CH$_2$CO.Y$_D$.Apc.GDCGGC$_{Acm}$GC$_{Acm}$GGC.amide)$_3$—TSEA | 4596 | 99$^4$ | 9.2, 11.6$^5$ |
| acetyl-RGDC.amide | 490 | 94$^3$ | 8.5$^5$ |
| (GPRPPPGGC$_{Acm}$GC$_{Acm}$GGC.amide)$_3$—TSEA | 4454$^a$ | 100$^4$ | 9.1$^5$ |
| (CH$_2$CO.Y$_D$Apc.GDCGGC$_{Acm}$GC$_{Acm}$GGC.amide)$_2$—[BAT—BS] | 3409$^a$ | 98$^3$ | 10.3$^5$ |
| Pic.GC$_{Acm}$PSPSPIHPAHHKRDRRQ.amide | 2351 | 94$^6$ | 11.2$^2$ |
| CH$_2$CO.YIGSRCGC$_{Acm}$GC$_{Acm}$.amide | 1199 | 94$^2$ | 16.8$^2$ |
| GRGDGGFC$_{Acm}$ | 839 | N.D. | N.D. |
| C$_{Acm}$GGGRGDF | 839 | 99$^7$ | 15.7–17.3$^2$ |
| GRGDGGC$_{Acm}$ | 692 | 98$^2$ | 14.1, 14.4$^2$ |
| ma$_{Bz}$-GGGRGDF | 843 | 100$^2$ | 16.7$^2$ |
| ma$_{Acm}$-GGGRGDF | 810 | 100$^7$ | 16.1$^2$ |
| CH$_2$CO.Y$_{D,Apc}$.GDCGGC$_{Acm}$GC$_{Acm}$GGC$_{NES}$.amide | 1517 | N.D. | N.D. |
| CH$_2$CO.Y$_{D,Apc}$.GDCKGC$_{Acm}$GC$_{Acm}$GGC.amide | 1485 | N.D. | N.D. |
| CRIARGDWNDDYC | 1587 | N.D. | N.D. |
| CKFFARTVCRIARGDWNDDYCTGKSSDC | 3329 | N.D. | N.D. |
| (CH$_2$CO.Y$_{D,Apc}$.GDCGGC$_{Acm}$GC$_{Acm}$GGC.amide)$_2$—BSH | 3062 | 100$^4$ | 11.5$^4$ |
| (CH$_2$CO.Y$_{D,Apc}$.GDCKGC$_{Acm}$GC$_{Acm}$GGC.amide)$_3$—BAT—BS | 3552 | N.D. | N.D. |
| CH$_2$CO.Y$_D$RGDCDGGC$_{Acm}$GC$_{Acm}$.amide | 1287 | 96$^2$ | 11.6, 11.9$^2$ |
| [BAT]G.Apc.GDV.Apc.GDFK.amide | 1432 | 96$^4$ | 17.5$^2$ |
| (CH$_2$CO.Y$_D$Apc.GDCKGC$_{Acm}$GC$_{Acm}$GGC.amide)$_2$—BSME | 3163$^a$ | 98$^4$ | 9.6$^5$ |

*Superscripts refer to the following labeling conditions:
1. The peptide is dissolved in 50 mM potassium phosphate buffer (pH 7.4) and labeled at room temperature.
2. The peptide is dissolved in 50 mM potassium phosphate buffer (pH 7.4) and labeled at 100° C.
3. The peptide is dissolved in water and labeled at room temperature.
4. The peptide is dissolved in water and labeled at 100° C.

TABLE I-continued

5. The peptide is dissolved in 50 mM potassium phosphate buffer (pH 6.0) and labeled at 100° C.
6. The peptide is dissolved in 50 mM potassium phosphate buffer (pH 5.0) and labeled at room temperature.
7. The peptide is dissolved in a 50:50 mixture of ethanol/water and labeled at 100° C.

**HPLC methods (indicated by superscript after $R_T$):
general:   solvent A = 0.1% $CF_3COOH/H_2O$
        solvent $B_{70}$ = 0.1% $CF_3COOH/70\% CH_3CH/H_2O$
        solvent $B_{90}$ = 0.1% $CF_3COOH/90\% CH_3CN/H_2O$
        solvent flow rate = 1 mL/min Vydak column = Vydak 218TP54 RP-18, $5\mu$ × 220 mm × 4.6 mm analytical column with guard column
Brownlee column = Brownlee Spheri-5 RP-18, $5\mu$ × 220 mm × 4.6 mm column
Waters column = Waters Delta-Pak C18, $5\mu$ × 150 mm × 3.9 mm column Method 1: Brownlee column   100% A to 100% $B_{70}$ in 10 min
Method 2: Vydak column      100% A to 100% $B_{90}$ in 10 min
Method 3: Vydak column      100% A to 100% $B_{70}$ in 10 min
Method 4: Waters column     100% A to 100% $B_{90}$ in 20 min
Method 5: Waters column     100% A to 100% $B_{90}$ in 10 min

***Confirmed by sodium dodecyl sulfate-polyacrylamide gel electrophoresis
****Confirmed by binding the peptide to an affinity column
Single-letter abbreviations for amino acids can be found in G. Zubay, Biochemistry (2d, ed.), 1988 (MacMillen Publishing: New York) p. 33;
underlining indicates the formation of a thiol linkage between the linked amino acids of derivative groups;
peptides are linked to BSH, ETAC, BSME, TSEA or [BAT—BS] linkers via the free thiol moiety of the unprotected cysteine residue (C) in each peptide;
Ac = acetyl;
Bz = benzoyl;
Pic = picolinoyl(pyridine-2-carbonyl);
Acm = acetamidomethyl;
Mob = 4-methoxybenzyl;
Apc = L-[S-(3-aminopropyl)cysteine;
Hly = homolysine;
$F_D$ = D-phenylalanine;
$Y_D$ = D-tyrosine;
ma = 2-mercaptoacetic acid;
mmp = 2-mercapto-2-methylpropionic acid;
BAT = $N^6,N^9$-bis(2-mercapto-2-methylpropyl)-6,9-diazanonanoic acid;
ETAC = 4-(O—$CH_2CO$—Gly—Gly—Cys.amide)acetophenone;
BAT—BS = N-[2-N__,N__-bis(2-succinimidoethy)aminoethyl]-$N^6,N^9$-bis(2-mercapto-2-methylpropyl)-6,9-diazanonanamide;
BSME = bis-succinimidomethylether;
TSEA = tris-(2-succinimidoethyl)amine;
NES = N-ethylsuccinimide;
BSH = 1,6-bis-succinimidohexane
$^a$ = confirmed by electrospray mass spectrometry [ESMS]

B. 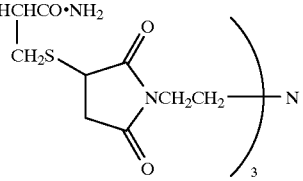

C. 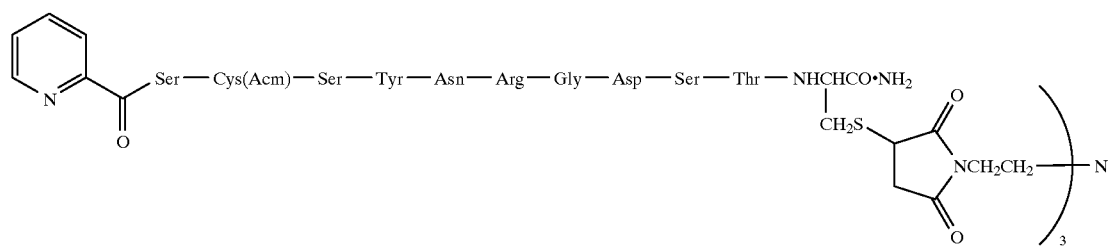

D. 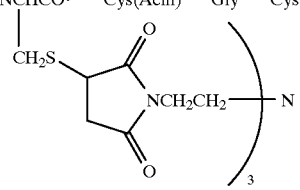

TABLE I-continued

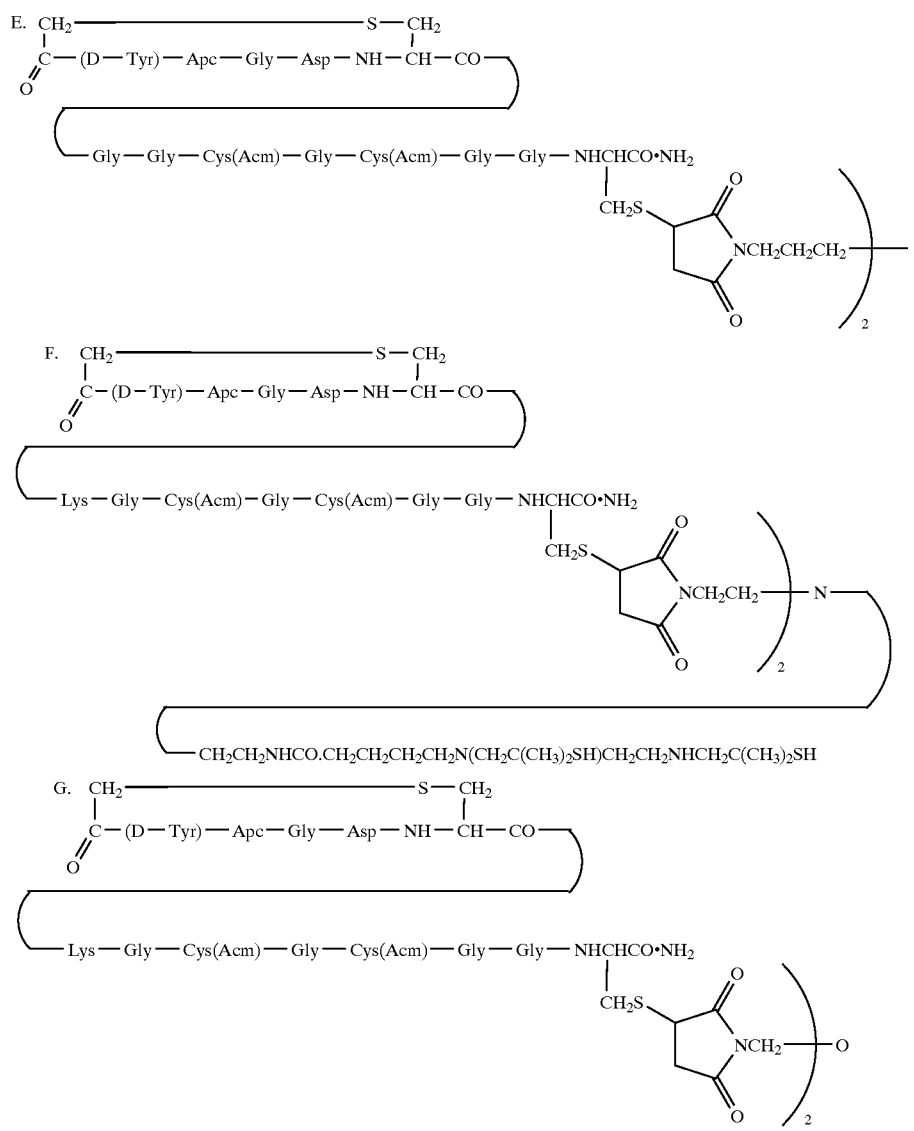

EXAMPLE 3

Platelet Aggregation Inhibition Assays

Platelet aggregation studies were performed essentially as described by Zucker (1989, Methods in Enzymol. 169: 117–133). Briefly, platelet aggregation was assayed with or without putative platelet aggregation inhibitory compounds using fresh human platelet-rich plasma, comprising 300,000 platelets per microliter. Platelet aggregation was induced by the addition of a solution of adenosine diphosphate to a final concentration of 10 to 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 µg/mL. The concentration of inhibitor that reduced the extent of platelet aggregation by 50% (defined as the $IC_{50}$) was determined from plots of inhibitor concentration versus extent of platelet aggregation. An inhibition curve for peptide RGDS was determined for each batch of platelets tested as a positive control.

The results of these experiments are shown in Table I. In Table I, the compounds tested are as follows:

P97=GRGDVRGDFKC$_{Acm}$GC$_{Acm}$amide

P32=C$_{Acm}$GC$_{Acm}$RRRRRRRRRGDV

P143=CH$_2$CO—Y$_D$RGDCGGC$_{Acm}$GC$_{Acm}$amide

P245=CH$_2$CO—Y$_D$.Apc.GDCGGC$_{Acm}$GC$_{Acm}$GGF$_D$PRPGamide

P98=GRDGVRGDFC$_{Acm}$GC$_{Acm}$amide

P81=CH$_2$CO—Y$_D$RGDCC$_{Acm}$GC$_{Acm}$amide

P154=CH$_2$CO—Y$_D$ApcGDCGGGC$_{Acm}$GC$_{Acm}$amide

P381=(CH$_2$CO—Y$_D$ApcGDCKGC$_{Acm}$GC$_{Acm}$GGC-amide)$_2$—BSME

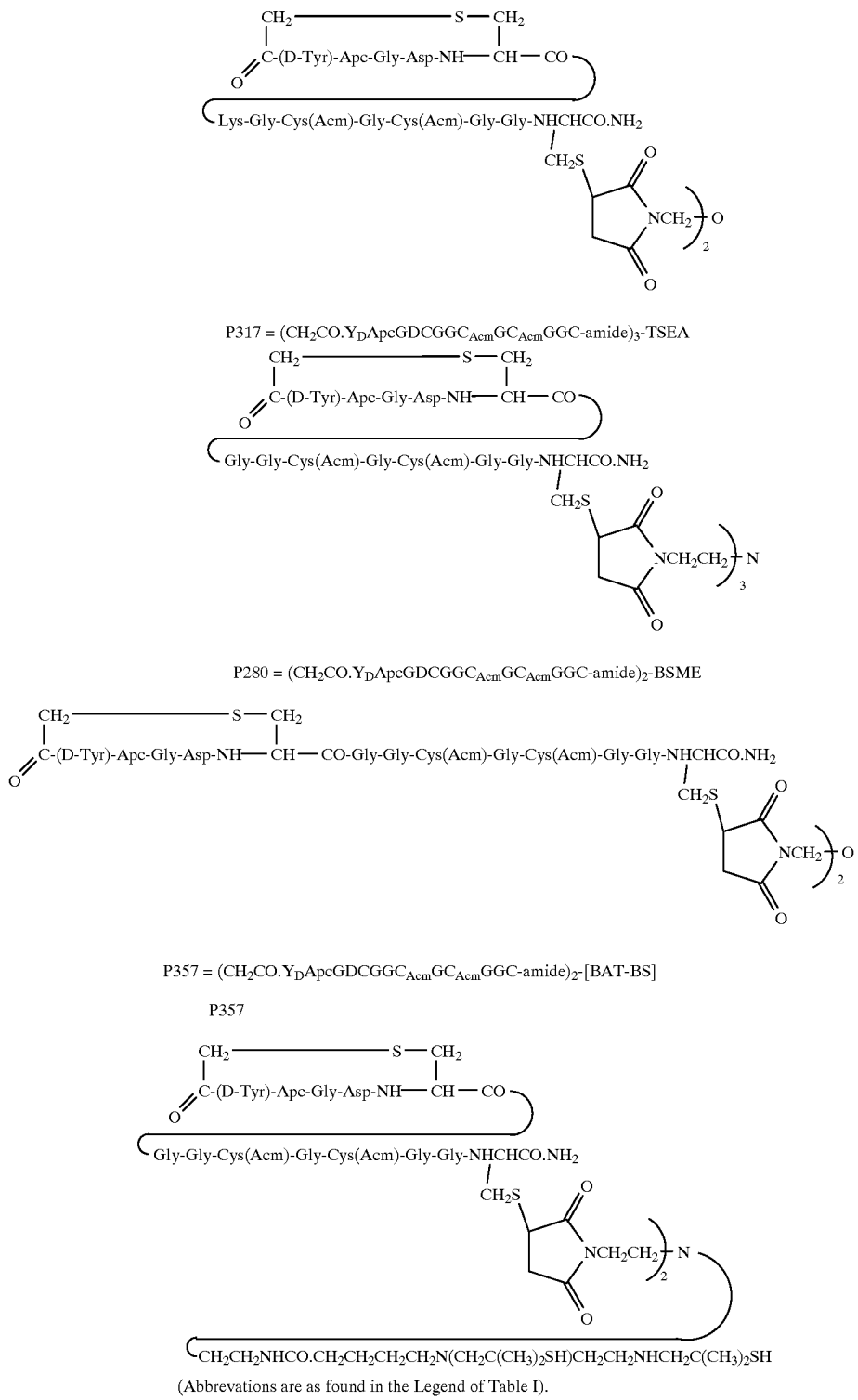
(Abbrevations are as found in the Legend of Table I).
These results demonstrate that peptide reagents of this invention bind with high affinity to activated platelets, in many cases with higher affinity than the naturally-occurring sequence RGDS.

TABLE II

| Peptides | IC$_{50}$ ($\mu$M)* |
|---|---|
| P317 | 0.036 |
| P381 | 0.035 |
| P357 | 0.081 |
| P280 | 0.090 |
| P154 | 0.3 |
| P245 | 0.5 |
| P143 | 1.3 |
| P97 | 8 |
| P98 | 15 |
| P81 | 25 |
| P32 | 26 |
| RGDS | 150–250 |

*concentration of reagent that inhibits by 50% the aggregation of human platelets in platelet-rich plasma induced to aggregate by the addition of adenosine diphosphate (ADP).

EXAMPLE 4
In Vivo Imaging of Deep Vein Thrombosis Using a Tc-99m Labeled Peptide in a Canine Model Mongrel dogs (25–35 lb., fasted overnight) were sedated with a combination of ketamine and aceprozamine intramuscularly and then anesthetized with sodium pentabarbital intravenously. In each animal, an 18-gauge angiocath was inserted in the distal half of the right femoral vein and an 8 mm Dacron®-entwined stainless steel embolization coil (Cook Co., Bloomington Ind.) was placed in the femoral vein at approximately mid-femur. The catheter was removed, the wound sutured and the placement of the coil documented by X-ray. The animals were then allowed to recover overnight.

One day following coil placement, each animal was re-anesthetized, intravenous saline drips placed in each foreleg and a urinary bladder catheter inserted to collect urine. The animal was placed supine under a gamma camera which was equipped with a low-energy, all purpose collimator and photopeaked for Tc-99m.

Tc-99m labeled peptide [185–370 mBq (5–10 mCi) Tc-99m] was injected sequentially into one foreleg intravenous line at its point of insertion. The second line was maintained for blood collection.

Gamma camera imaging was started simultaneously with injection. Anterior images over the heart were acquired as a dynamic study (10 sec image acquisitions) over the first 10 min, and then as static images at 1, 2, 3 and 4 h post-injection. Anterior images over the legs were acquired for 500,000 counts or 20 min (whichever was shorter), at approximately 10–20 min, and at approximately 1, 2, 3 and 4 h post-injection. Leg images were collected with a lead shield placed over the bladder.

Following the final image, each animal was deeply anesthetized with pentobarbital. Two blood samples were collected on a cardiac puncture using a heparinized syringe followed by a euthanasing dose of saturated potassium chloride solution administered by intercardiac or bolus intravenous injection. The femoral vein containing the thrombus, a similar section of vein of the contralateral (control) leg, sections of the vessel proximal to the thrombus and samples of thigh muscle were then carefully dissected out. The thrombus, coil and coil Dacron fibres were then dissected free of the vessel. The thrombus, saline-washed vessel samples, coil and coil Dacron fibres were separated, and each sample was placed in a pre-weighed test tube. The samples were weighed and counted in a gamma well counter in the Tc-99m channel, along with known fractions of the injected doses.

Fresh thrombus weight, percent injected dose (%ID)/g in the thrombus and blood obtained just prior to euthanasia and thrombus/blood and thrombus/muscle ratios were determined. From the computer-stored images, thrombus/background ratios were determined by analysis of the counts/pixel measured in regions-of-interest (ROI) drawn over the thrombus and adjacent muscle. Tissue data from these experiments are shown in the following Table. Scintigraphic images showing the location of venous thrombi in vivo detected using Tc-99m labeled peptide are shown in FIG. 1.

These results demonstrate that deep vein thrombi can be rapidly and efficiently located in vivo using Tc-99m labeled reagents of the invention. Localization was clearly established within 1 h post-injection and persisted, with increasing contrast and focal definition, over nearly 4 h post-injection.

It should be understood that the foregoing disclosure emphasizes certain specific embodiments of the invention and that all modifications or alternatives equivalent thereto are within the spirit and scope of the invention as set forth in the appended claims.

TABLE III

| Peptide | Thrombus/Background | % ID/g Thrombus | % ID/g Blood | Thrombus/Blood | Thrombus/Muscle |
|---|---|---|---|---|---|
| P317 (n = 4)[a] | N.D. | 0.0035 | 0.0011 | 3.8 ± 2.2 | 16 ± 10 |
| P280 (n = 6) | 2.3 ± 0.4 | 0.0059 | 0.0012 | 4.4 ± 1.8 | 11 ± 7 |
| P357 (n = 9) | N.D. | 0.019 | 0.0028 | 11 ± 7 | 21 ± 14 |

Values shown are the average ± the standard deviation from the mean;
[[a]n = number of experiments performed with this peptide]

What is claimed is:

1. A reagent for preparing a scintigraphic imaging agent for imaging a thrombus within a mammalian body comprising a specific binding compound capable of binding to at least one component of a thrombus, covalently linked to a technetium-99m binding moiety, wherein the technetium-99m binding moiety has the formula:

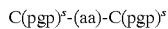

wherein $C(pgp)^s$ is a cysteine having a protect thiol group and (aa) is an amino acid.

2. The reagent of claim 1 that is radiolabeled with technetium-99m.

3. The reagent of claim 1 wherein the specific binding compound and $C(pgp)^s$-(aa)-$C(pgp)^s$ are covalently linked through from about one to about 20 amino acids.

4. The reagent of claim 1 wherein each of the protected cysteines comprising the technetium-99m binding moiety has a protecting group of the formula

—CH$_2$—NH—CO—R wherein R is a lower alkyl having 1 to 6 carbon atoms, 2-,3-,4-pyridyl, phenyl, or phenyl substituted with lower alkyl, hydroxy, lower alkoxy, carboxy, or lower alkoxycarbonyl.

5. The reagent of claim 1 wherein $C(pgp)^s$-(aa)-$C(pgp)^s$ has the formula:

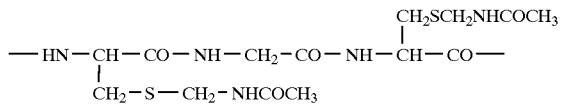

6. The reagent of claim 1 wherein the specific binding compound is a peptide comprising 4 to 100 amino acids.

7. The reagent of claim 6 selected from the group consisting of:

-continued

CH$_2$CO.Y$_D$.Apc.GDC.Apc.GDFKC$_{Acm}$GC$_{Acm}$.amide.

CH$_2$CO.Y$_D$.Apc.GDCKGC$_{Acm}$GC$_{Acm}$.amide.
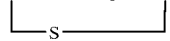

CH$_2$CO.Y$_D$.Apc.GDCGGC$_{Acm}$GC$_{Acm}$GGC.amide.

CH$_2$CO.Y$_D$.Apc.GDCGGC$_{Acm}$GC$_{Acm}$GGC$_{NES}$.amide.

(CH$_2$CO.Y$_D$.Apc.GDCGGC$_{Acm}$GC$_{Acm}$GGC.amide)$_3$-TSEA.

CH$_2$CO.Y$_D$.Apc.GDCGGC$_{Acm}$GC$_{Acm}$GGF$_D$PRPG.amide.
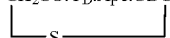

CH$_2$CO.Y$_D$RGDCGGC$_{Acm}$GC$_{Acm}$.amide.
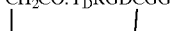

CH$_2$CO.Y$_D$KGDCGGGC$_{Acm}$GC$_{Acm}$.amide.
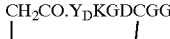

CH$_2$CO.Y$_D$.Apc.GDCKGC$_{Acm}$GC$_{Acm}$GCC.amide.
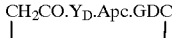

acetyl-C$_{Acm}$GC$_{Acm}$CNP.Apc.GDC.

(CH$_2$CO.Y$_D$.Apc.GDCGGC$_{Acm}$GC$_{Acm}$GGC.amide)$_2$-BSH.
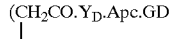

(CH$_2$CO.Y$_D$.Apc.GDCGGC$_{Acm}$GC$_{Acm}$GGC.amide)$_2$-BSME.

(CH$_2$CO.Y$_D$.Apc.GDCKGC$_{Acm}$GC$_{Acm}$GGC.amide)$_2$-BSME.

(CH$_2$CO.Y$_D$.Apc.GDCGGC$_{Acm}$GC$_{Acm}$GGC.amide)$_2$-{BAT-BS}.
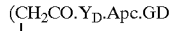

(CH$_2$CO.Y$_D$.Apc.GDCKGC$_{Acm}$GC$_{Acm}$GGC.amide)$_2$-{BAT-BS}.
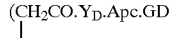

C$_{Acm}$GC$_{Acm}$GGRGDS,
C$_{Acm}$GC$_{Acm}$GGRGDGGRGDS,
C$_{Acm}$GC$_{Acm}$GGRGDGGRGDGGRGDS,
C$_{Acm}$GC$_{Acm}$RRRRRRRRRGDV,
GRGDVKC$_{Acm}$GC$_{Acm}$.amide,
GRGDVC$_{Acm}$GC$_{Acm}$.amide,
GRGDVRGDFKC$_{Acm}$GC$_{Acm}$.amide,
GRGDVRGDFC$_{Acm}$GC$_{Acm}$.amide,
acetyl-G.Apc.GDV.Apc.GDFKC$_{Acm}$GC$_{Acm}$.amide,
G.Apc.GCV.Apc.GDFKC$_{Acm}$GC$_{Acm}$.amide,
G.Aklpc.GDVKC$_{Acm}$GC$_{Acm}$.amide,
(CC$_{Acm}$GC$_{Acm}$GGRGDS)$_3$—TSEA,
C$_{Acm}$GC$_{Acm}$NDGDFEEIPEEYLQ,
C$_{Acm}$GC$_{Acm}$GGF$_D$PRPGGGGNGDFEEIPEEYL,
C$_{Acm}$GC$_{Acm}$GGF$_D$PRPGamide,
{(GPRP)$_2$K}$_2$KC$_{Acm}$GC$_{Acm}$.amide,
(GPRVVERHQSA)$_2$KC$_{Acm}$GC$_{Acm}$.amide, (GPRPC$_{Acm}$GC$_{Acm}$C)$_3$—TSEA,
[GPRPPPGGC$_{Acm}$GC$_{Acm}$GGC]$_3$—TSEA, CH$_2$CO.YIGSRCGC$_{Acm}$GC$_{Mob}$.
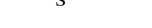

CH$_2$CO.YIGSRCGC$_{Acm}$GC$_{Acm}$.amide.

acetyl-RRARGDDLDC$_{Acm}$GC$_{Acm}$.amide, and
PSPSPIHPAHHKRDRRQC$_{Acm}$GC$_{Acm}$.amide.

8. A complex formed by reacting the reagent of claim 1 with technetium-99m in the presence of a reducing agent.

9. The complex of claim 8, wherein the reducing agent is selected from the group consisting of a dithionite ion, a stannous ion and a ferrous ion.

10. A complex formed by labeling the reagent of claim 1 with technetium-99m by ligand exchange of a prereduced technetium-99m complex.

11. A kit for preparing a radiopharmaceutical preparation, said kit comprising a sealed vial containing a predetermined quantity of the reagent of claim 1 and a sufficient amount of reducing agent to label the reagent with technetium-99m.

12. A method for labeling a reagent according to claim 1 comprising reacting the reagent with technetium-99m in the presence of a reducing agent.

13. The method of claim 12, wherein the reducing agent is selected from the group consisting of a dithionite ion, a stannous ion and a ferrous ion.

14. A method for imaging a thrombus within a mammalian body comprising the steps of administering an effective diagnostic amount of the technetium-99m radiolabeled reagent of claim 2 to an animal and detecting the radiolabeled reagent localized at the site of a thrombus.

15. The reagent according to claim 1 wherein the specific-binding peptide is chemically synthesized in vitro.

16. The reagent according to claim 15 wherein the specific-binding peptide is synthesized by solid phase peptide synthesis.

17. The reagent according to claim 15 wherein the radiolabel-binding moiety is covalently linked to the specific-binding peptide during in vitro chemical synthesis.

18. The reagent according to claim 17 wherein the radiolabel-binding moiety is covalently linked to the specific-binding peptide during solid phase peptide synthesis.

19. A composition of matter comprising a reagent selected from the group consisting of:

CH$_2$CO.Y$_D$RGDCC$_{Acm}$GC$_{Acm}$.amide.
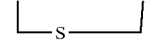

CH$_2$CO.Y$_D$RGDCWGGC$_{Acm}$GC$_{Acm}$.amide.
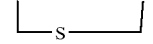

CH$_2$CO.Y$_D$RGDCFGGC$_{Acm}$GC$_{Acm}$.amide.

CH$_2$CO.Y$_D$RGDCGGGC$_{Acm}$GC$_{Acm}$.amide.

CH$_2$CO.Y$_D$RGDCDGGC$_{Acm}$GC$_{Acm}$.amide.
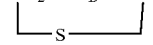

79
-continued

CH$_2$CO.Y$_D$.Apc.GDCGGGC$_{Acm}$GC$_{Acm}$.amide.
|—S———|

CH$_2$CO.Y$_D$.Apc.GDC.Apc.GDFKC$_{Acm}$GC$_{Acm}$.amide.
|—S————————|

CH$_2$CO.Y$_D$.Apc.GDCKGC$_{Acm}$GC$_{Acm}$.amide.
|—S————|

CH$_2$CO.Y$_D$.Apc.GDCGGC$_{Acm}$GC$_{Acm}$GGC.amide.
|—S———|

CH$_2$CO.Y$_D$.Apc.GDCGGC$_{Acm}$GC$_{Acm}$GGC$_{NES}$.amide.
|—S———|

(CH$_2$CO.Y$_D$.Apc.GDCGGC$_{Acm}$GC$_{Acm}$GGC.amide)$_3$-TSEA.
|—S———|

CH$_2$CO.Y$_D$.Apc.GDCGGC$_{Acm}$GC$_{Acm}$GGF$_D$PRPG.amide.
|—S———|

CH$_2$CO.Y$_D$RGDCGGC$_{Acm}$GC$_{Acm}$.amide.
|—S———|

CH$_2$CO.Y$_D$KGDCGGGC$_{Acm}$GC$_{Acm}$.amide.
|—S———|

CH$_2$CO.Y$_D$.Apc.GDCKGC$_{Acm}$GC$_{Acm}$GCC.amide.
|—S————| acetyl-C$_{Acm}$GC$_{Acm}$CNP.Apc.GDC.
      |———S-S———|

(CH$_2$CO.Y$_D$.Apc.GDCGGC$_{Acm}$GC$_{Acm}$GGC.amide)$_2$-BSH.
|—S———|

(CH$_2$CO.Y$_D$.Apc.GDCGGC$_{Acm}$GC$_{Acm}$GGC.amide)$_2$-BSME.
|—S———|

(CH$_2$CO.Y$_D$.Apc.GDCKGC$_{Acm}$GC$_{Acm}$GGC.amide)$_2$-BSME.
|—S————|

(CH$_2$CO.Y$_D$.Apc.GDCGGC$_{Acm}$GC$_{Acm}$GGC.amide)$_2$-{BAT-BS}
|—S———|

(CH$_2$CO.Y$_D$.Apc.GDCKGC$_{Acm}$GC$_{Acm}$GGC.amide)$_2$-{BAT-BS}
|—S————|

C$_{Acm}$GC$_{Acm}$GGRGDS,
C$_{Acm}$GC$_{Acm}$GGRGDGGRGDS,
C$_{Acm}$GC$_{Acm}$GGRGDGGRGDGGRGDS,
C$_{Acm}$GC$_{Acm}$RRRRRRRRRGDV,
GRGDVKC$_{Acm}$GC$_{Acm}$.amide,
GRGDVC$_{Acm}$GC$_{Acm}$.amide,
GRGDVRGDFKC$_{Acm}$GC$_{Acm}$.amide,
GRGDVRGDFC$_{Acm}$GC$_{Acm}$.amide,
acetyl-G.apc.GDV.Apc.GDFKC$_{Acm}$GC$_{Acm}$.amide,
G.Apc.GDV.Apc.GDFKC$_{Acm}$GC$_{Acm}$.amide,
G.Apc.GDVKC$_{Acm}$GC$_{Acm}$.amide,
(CC$_{Acm}$GC$_{Acm}$GGRGDS)$_3$—TSEA,
C$_{Acm}$GC$_{Acm}$NDGDFEEIPEEYLQ,
C$_{Acm}$GC$_{Acm}$GGF$_D$PRPGGGGNGDFEEIPEEYL,

80

C$_{Acm}$GC$_{Acm}$GGF$_D$PRPGamide,
{(GPRP)$_2$K}$_2$KC$_{Acm}$GC$_{Acm}$.amide,
(GPRVVERHQSA)$_2$KC$_{Acm}$GC$_{Acm}$.amide,
(GPRPC$_{Acm}$GC$_{Acm}$C)$_3$—TSEA, {GPRPPPGGC$_{Acm}$GC$_{Acm}$GGC}$_3$-TSEA.

CH$_2$CO.YIGSRCGC$_{Acm}$GC$_{Mob}$.
|—S——|

CH$_2$CO.YIGSRCGC$_{Acm}$GC$_{Acm}$.amide.
|—S——|

20. The reagent of claim 1 wherein the reagent further comprises a polyvalent linking moiety covalently linked to a multiplicity of specific binding compounds and also covalently linked to a multiplicity of radiolabel-binding moieties to comprise a reagent for preparing a multimeric polyvalent scintigraphic imaging agent; wherein the molecular weight of the multimeric polyvalent scintigraphic imaging agent is less than about 20,000 daltons.

21. The reagent of claim 20 wherein the polyvalent linking moiety is bis-succinimidylmethylether, 4-(2,2-dimethylacetyl)benzoic acid, N-[2-(N',N'-bis(2-succinimidoethyl)aminoethyl)]—N$^6$,N$^9$-bis(2-methyl-2-mercaptopropyl)-6,9-diazanonanamide, tris (succinimidylethyl)amine, bis-succinimidohexane, or 4-(O—CH$_2$CO—Gly—Gly—Cys.amide)acetophenone.

22. A reagent for preparing a thrombus imaging agent for imaging a thrombus within la mammalian body comprising a specific binding peptide having an amino acid sequence of 40 to 100 amino acids and a technetium-99m binding moiety covalently linked to the specific binding peptide, wherein the peptide is a ligand for a polymerization site of fibrin, having an amino acid sequence comprising multiple copies of the sequence (glycyl-prolyl-arginyl-prolyl).

23. A reagent for preparing a thrombus imaging agent for imaging a thrombus within a mammalian body comprising a specific binding peptide having an amino acid sequence of 4 to 100 amino acids and a technetium-99m binding moiety covalently linked to the specific binding peptide, wherein the reagent has the formula:

{(GPRP)$_2$K}$_2$KC$_{Acm}$GC$_{Acm}$.amide,
(GPRVVERHQSA)$_2$KC$_{Acm}$GC$_{Acm}$.amide,
(GPRPC$_{Acm}$GC$_{Acm}$C)$_3$—TSEA,
{GPRPPPGGC$_{Acm}$GC$_{Acm}$GGC}$_3$—TSEA,
acetyl-CNP.Apc.GDC,
{BAT}.Hly.GDP.Hly.GDF.amide,
{BAT}G.Apc.GDV.Apc.GDFK.amide, CH$_2$CO.Y$_D$RGDCC$_{Acm}$GC$_{Acm}$.amide,
   \\S/

CH$_2$CO.Y$_D$RGDCWGGC$_{Acm}$GC$_{Acm}$.amide,
   \\S/

CH$_2$CO.Y$_D$RGDCFGGC$_{Acm}$GC$_{Acm}$.amide,
   \\S/

CH$_2$CO.Y$_D$RGDCGGGC$_{Acm}$GC$_{Acm}$.amide,
   \\S/

-continued

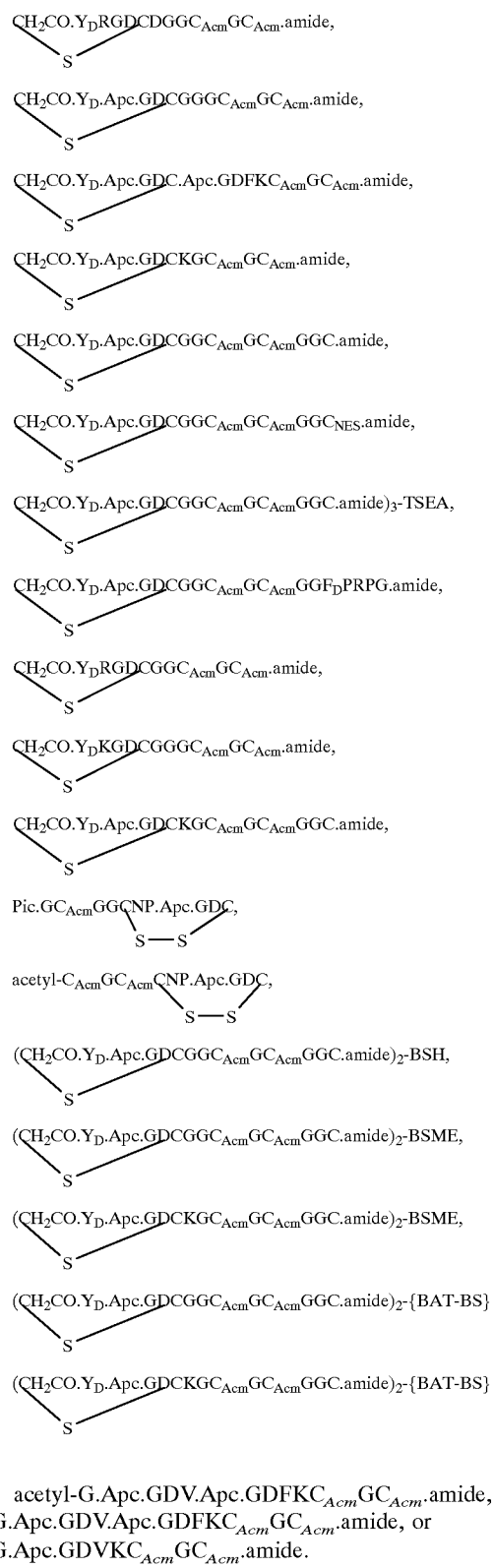

acetyl-G.Apc.GDV.Apc.GDFKC$_{Acm}$GC$_{Acm}$.amide,
G.Apc.GDV.Apc.GDFKC$_{Acm}$GC$_{Acm}$.amide, or
G.Apc.GDVKC$_{Acm}$GC$_{Acm}$.amide.

24. The reagent of claim 22, that is radiolabled with technetium-99m.

25. The reagent according to claim 22 wherein the specific-binding peptide and the technetium-99m binding moiety are covalently linked through from about to about 20 amino acids.

26. A complex formed by reacting the reagent according to claim 22 with technetium-99m in the presence of a reducing agent.

27. The complex of claim 26, wherein the reducing agent is selected from the group consisting of a dithionite ion, a stannous ion and a ferrous ion.

28. A complex formed by labeling the reagent according to claim 22 with technetium-99m by ligand exchange of a prereduced technetium-99m complex.

29. A composition of matter comprising the reagent according to claim 22 and a stannous ion.

30. A kit for preparing a radiopharmaceutical preparation, said kit comprising a sealed vial containing a predetermined quantity of a reagent according to claim 22 and a sufficient amount of reducing agent to label said reagent with technetium-99m.

31. A method for labeling a reagent according to claim 22 comprising reacting the reagent with technetium-99m in the presence of a reducing agent.

32. The method of claim 31, wherein the reducing agent is selected from the group consisting of a dithionite ion, a stannous ion and a ferrous ion.

33. A method for imaging a thrombus within a mammalian body comprising the steps of administering an effective diagnostic amount of the technetium-99m radiolabeled reagent of claim 26 to an animal and detecting the radiolabeled reagent localized at the site of a thrombus.

34. The reagent according to claim 22 wherein the specific-binding peptide is chemically synthesized in vitro.

35. The specific-binding peptide according to claim 34 wherein the peptide is synthesized by solid phase peptide synthesis.

36. The reagent according to claim 34 wherein the technetium-99m binding moiety is covalently linked to the peptide during in vitro chemical synthesis.

37. The reagent according to claim 36, wherein the technetium-99m binding moiety is covalently linked to the peptide during solid phase peptide synthesis.

38. The reagent of claim 22 wherein the reagent further comprises a polyvalent linking moiety covalently linked to a multiplicity of specific binding compounds and also covalently linked to a multiplicity of radiolabel-binding moieties to comprise a reagent for preparing a multimeric polyvalent scintigraphic imaging agent, wherein the molecular weight of the multimeric polyvalent scintigraphic imaging agent is less than about 20,000 daltons.

39. The reagent of claim 38 wherein the polyvalent linking moiety is bis-succinimidylmethylether, 4-(2,2-dimethylacetyl)benzoic acid, N-[2-(N',N'-bis(2-succinimidoethyl)aminoethyl)]—N$^6$,N$^9$-bis(2-methyl-2-mercaptopropyl)-6,9-diazanonanamide, tris (succinimidylethyl)amine, bis-succinimidohexane, or 4-(O—CH$_2$CO—Gly—Gly—Cys.amide)acetophenone.

* * * * *